US010744289B2

(12) United States Patent
Lynch et al.

(10) Patent No.: US 10,744,289 B2
(45) Date of Patent: Aug. 18, 2020

(54) FRAME AND VENT ASSEMBLY FOR MASK ASSEMBLY

(71) Applicant: ResMed Pty Ltd, Bella Vista, New South Wales (AU)

(72) Inventors: Susan Robyn Lynch, Maitland (AU); Philip Thomas Stallard, Sydney (AU); Scott Alexander Howard, Sydney (AU); Joshua Adam Gudiksen, Sydney (AU); Murray William Lee, Sydney (AU); Matthew Eves, Sydney (AU); Melanie Lucia Cariola, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 983 days.

(21) Appl. No.: 14/959,619

(22) Filed: Dec. 4, 2015

(65) Prior Publication Data
US 2016/0082216 A1 Mar. 24, 2016

Related U.S. Application Data

(62) Division of application No. 12/312,308, filed as application No. PCT/AU2007/001749 on Nov. 14, 2007, now Pat. No. 9,254,370.

(60) Provisional application No. 60/858,700, filed on Nov. 14, 2006.

(51) Int. Cl.
*A61M 16/06* (2006.01)
*A61M 16/00* (2006.01)
*A61M 16/08* (2006.01)

(52) U.S. Cl.
CPC .... *A61M 16/0633* (2014.02); *A61M 16/0057* (2013.01); *A61M 16/06* (2013.01); *A61M 16/0683* (2013.01); *A61M 16/0816* (2013.01); *A61M 16/0875* (2013.01); *A61M 2016/0661* (2013.01); *A61M 2205/42* (2013.01)

(58) Field of Classification Search
CPC .............. A61M 16/06; A61M 16/0633; A61M 16/0057; A61M 16/0683; A61M 16/0816; A61M 16/0875; A61M 2016/0661; A61M 2205/42
USPC ............ 128/203.29, 205.25, 206.12, 206.21, 128/206.28, 207.13
See application file for complete search history.

(56) References Cited

U.S. PATENT DOCUMENTS

| | | |
|---|---|---|
| 2,603,215 A | 7/1952 | Arnow |
| 2,738,788 A | 3/1956 | Matheson et al. |
| 2,742,821 A | 4/1956 | Sweetman |
| 2,763,263 A | 9/1956 | Ellman |
| 3,118,445 A | 1/1964 | Marius |

(Continued)

FOREIGN PATENT DOCUMENTS

| | | |
|---|---|---|
| GB | 880824 | 10/1961 |
| WO | WO 1998/034665 | 8/1998 |

(Continued)

OTHER PUBLICATIONS

U.S. Appl. No. 10/781,929, filed Feb. 2004, Gunaratnam et al.
(Continued)

*Primary Examiner* — Sundhara M Ganesan
(74) *Attorney, Agent, or Firm* — Nixon & Vanderhye P.C.

(57) ABSTRACT

A nasal or full-face mask frame includes a main body and a vent assembly provided to the main body. The vent assembly includes a plurality of holes arranged in at least one column. The holes are positioned on a relatively flat and/or non-recessed portion of the main body.

64 Claims, 27 Drawing Sheets

(56) References Cited

U.S. PATENT DOCUMENTS

| | | | |
|---|---|---|---|
| 3,228,610 | A | 1/1966 | Quaas et al. |
| 3,425,600 | A | 2/1969 | Abplanalp |
| 3,513,844 | A | 5/1970 | Smith |
| 3,633,575 | A | 1/1972 | Brumfield |
| 3,850,171 | A | 11/1974 | Ball et al. |
| 4,090,510 | A | 5/1978 | Segersten |
| 4,161,516 | A | 7/1979 | Bell |
| 4,328,797 | A | 5/1982 | Rollins et al. |
| 4,347,633 | A | 9/1982 | Gammons et al. |
| 4,424,106 | A | 1/1984 | Rossoshinsky et al. |
| 4,782,832 | A | 11/1988 | Trimble et al. |
| 4,856,508 | A | 8/1989 | Tayebi |
| 4,989,596 | A | 2/1991 | Macris et al. |
| 5,042,478 | A | 8/1991 | Kopala et al. |
| 5,195,773 | A | 3/1993 | Sawada et al. |
| 5,324,295 | A | 6/1994 | Shapiro |
| 5,431,158 | A | 7/1995 | Tirotta |
| 5,533,506 | A | 7/1996 | Wood |
| 5,656,523 | A | 8/1997 | Hodsen et al. |
| 5,683,293 | A | 11/1997 | Mohammed |
| 5,687,746 | A | 11/1997 | Rose et al. |
| 5,709,204 | A | 1/1998 | Lester |
| 5,724,965 | A | 3/1998 | Handke et al. |
| 5,740,649 | A | 4/1998 | Fuchs et al. |
| 5,962,349 | A | 10/1999 | Mizukami et al. |
| 6,012,455 | A | 1/2000 | Goldstein |
| 6,017,315 | A | 1/2000 | Starr et al. |
| 6,044,844 | A | 4/2000 | Kwok et al. |
| 6,074,446 | A | 6/2000 | Fujino |
| 6,077,152 | A | 6/2000 | Warehime |
| 6,082,356 | A | 7/2000 | Stradella |
| 6,119,694 | A | 9/2000 | Correa |
| 6,210,806 | B1 | 4/2001 | Hidaka et al. |
| 6,241,247 | B1 | 6/2001 | Sternberg et al. |
| 6,336,455 | B1 | 1/2002 | Howlett |
| 6,431,172 | B1 | 2/2002 | Bordewick |
| 6,378,518 | B1 | 4/2002 | Miekka et al. |
| 6,401,716 | B1 | 6/2002 | Sword et al. |
| 6,418,929 | B1 | 7/2002 | Norfleet |
| 6,561,190 | B1 | 5/2003 | Kwok |
| 6,561,191 | B1 | 5/2003 | Kwok |
| 6,581,594 | B1 | 6/2003 | Drew et al. |
| 6,595,215 | B2 | 7/2003 | Wood |
| 6,638,588 | B1 | 10/2003 | Bowen et al. |
| 6,691,707 | B1 | 2/2004 | Gunaratnam et al. |
| 6,851,425 | B2 | 2/2005 | Jaffre et al. |
| 7,207,335 | B2 | 4/2007 | Kwok et al. |
| D557,800 | S | 12/2007 | Hitchcock et al. |
| 7,318,437 | B2 | 1/2008 | Gunaratnam et al. |
| D587,800 | S | 3/2009 | Judson et al. |
| 7,686,800 | B2 | 3/2010 | Savage et al. |
| 7,827,990 | B1 | 11/2010 | Melidis et al. |
| 7,836,884 | B2 | 11/2010 | Wright |
| 7,845,354 | B2 | 12/2010 | Kwok et al. |
| 7,934,501 | B2 | 5/2011 | Fu et al. |
| 7,942,150 | B2 | 5/2011 | Guney et al. |
| 8,042,539 | B2 | 10/2011 | Chandran et al. |
| 8,122,886 | B2 | 2/2012 | Kwok et al. |
| 8,261,746 | B2 | 9/2012 | Lynch et al. |
| 8,297,283 | B2 | 10/2012 | Hitchcock et al. |
| 8,397,728 | B2 | 3/2013 | D'Souza et al. |
| 2001/0029948 | A1 | 10/2001 | Ingle et al. |
| 2002/0172566 | A1 | 11/2002 | Issler |
| 2003/0005931 | A1 | 1/2003 | Jaffre et al. |
| 2003/0005935 | A1 | 1/2003 | Kwok et al. |
| 2003/0075180 | A1 | 4/2003 | Raje et al. |
| 2003/0079751 | A1 | 5/2003 | Kwok |
| 2003/0196655 | A1 | 10/2003 | Ging |
| 2004/0022820 | A1 | 2/2004 | Anderson |
| 2004/0177850 | A1 | 9/2004 | Gradon et al. |
| 2004/0226566 | A1 | 11/2004 | Gunaratnam et al. |
| 2005/0011524 | A1 | 1/2005 | Thomlinson |
| 2005/0028822 | A1 | 2/2005 | Sleeper |
| 2005/0076913 | A1 | 4/2005 | Ho |
| 2005/0092326 | A1 | 5/2005 | Drew et al. |
| 2005/0126573 | A1 | 6/2005 | Jaffre et al. |
| 2005/0241644 | A1 | 11/2005 | Gunaratnam et al. |
| 2006/0042629 | A1 | 3/2006 | Geist |
| 2006/0118119 | A1 | 6/2006 | Berthon-Jones et al. |
| 2006/0174887 | A1 | 8/2006 | Chandran et al. |
| 2006/0196509 | A1 | 9/2006 | Drew et al. |
| 2006/0201514 | A1 | 9/2006 | Jones et al. |
| 2006/0254593 | A1 | 11/2006 | Chang |
| 2006/0266361 | A1 | 11/2006 | Hernandez |
| 2007/0044804 | A1 | 3/2007 | Matula et al. |
| 2007/0062536 | A1 | 3/2007 | McAuley et al. |
| 2007/0095350 | A1 | 5/2007 | Darkin et al. |
| 2007/0175480 | A1 | 8/2007 | Gradon et al. |
| 2007/0221226 | A1 | 9/2007 | Hansen et al. |
| 2009/0044810 | A1 | 2/2009 | Kwok |
| 2009/0139526 | A1 | 6/2009 | Melidis et al. |
| 2009/0151729 | A1 | 6/2009 | Judson et al. |
| 2009/0277452 | A1 | 11/2009 | Lubke et al. |
| 2010/0051034 | A1 | 3/2010 | Lynch et al. |
| 2010/0282265 | A1 | 11/2010 | Melidis et al. |
| 2011/0180071 | A1 | 7/2011 | Veliss et al. |
| 2011/0277771 | A1 | 11/2011 | Kwok et al. |

FOREIGN PATENT DOCUMENTS

| | | |
|---|---|---|
| WO | WO 00/013751 | 3/2000 |
| WO | WO 01/62326 A1 | 8/2001 |
| WO | WO 2002/066105 | 8/2002 |
| WO | WO 2004/030736 A1 | 4/2004 |
| WO | WO 2004/073778 | 9/2004 |
| WO | WO 2005/021075 A1 | 3/2005 |
| WO | WO 2005/079726 | 9/2005 |
| WO | WO 2006/069415 | 7/2006 |
| WO | WO 2006/074516 | 7/2006 |
| WO | WO 2006/074517 | 7/2006 |
| WO | WO 2007/041751 | 4/2007 |
| WO | WO 2007/045008 | 4/2007 |
| WO | WO 2007/053878 | 5/2007 |

OTHER PUBLICATIONS

U.S. Appl. No. 11/101,657, filed Apr. 2005, Gunaratnam et al.
U.S. Appl. No. 29/258,084, filed Apr. 2006, Judson et al.
U.S. Appl. No. 60/734,282, filed Nov. 2005, Judson et al.
U.S. Appl. No. 60/758,200, filed Jan. 2006, Judson et al.
U.S. Appl. No. 60/795,562, filed Apr. 2006, Scheiner et al.
U.S. Appl. No. 60/795,615, filed Apr. 2006, Smart et al.
U.S. Appl. No. 60/819,626, filed Jul. 2006, Judson et al.
U.S. Appl. No. 60/838,442, filed Aug. 2006, Judson et al.
Apr. 24, 2015 Application Under Regulation 168 for Extension of Time (1 pg.) and Notice of Opposition to Grant of Patent (Section 21) (2 pgs.).
Apr. 29, 2015 Extension of Time Granted in New Zealand Application No. 611284 (1 pg.).
Aug. 28, 2015 Opponent's Letter to the Applicant in corresponding New Zealand Application No. 611284.
Feb. 2, 2015 Office Action issued in U.S. Appl. No. 12/084,373 (10 pages).
Jan. 10, 2008 International Search Report issued in International Application No. PCT/AU2007/001749.
Jan. 11, 2011 Examination Report issued in New Zealand Application No. 567374.
Jan. 11, 2011 Examination Report issued in New Zealand Application No. 590211.
Jan. 9, 2007 International Search Report issued in International Application No. PCT/AU2006/001507.
Jun. 20, 2014 Office Action issued in U.S. Appl. No. 12/084,373 (41 pages).
Jun. 24, 2015 Amended Notice of Opposition to Grant of Patent in corresponding New Zealand Patent Application No. 611284.
Jun. 24, 2015 Statement of Case in corresponding New Zealand Patent Application No. 611284.
Mar. 25, 2013 Deadline for Counterstatement issued in New Zealand Application No. 590211 (8 pages).

(56) References Cited

OTHER PUBLICATIONS

Oct. 29, 2012 Proceeding Correspondence issued in New Zealand Application No. 590211 (3 pages).
Sep. 24, 2015 Office Action issued in U.S. Appl. No. 12/084,373.
Sep. 3, 2015 Decision of Assistant Commissioner issued in corresponding New Zealand Application No. 590211.
Mar. 28, 2016 Office Action issued in U.S. Appl. No. 12/084,373.
Gunaratnam, U.S. Appl. No. 29/213,882, filed May 2004.
Jan. 12, 2017 Letter to IPONZ and Marked-up Amended Statement of Case filed in New Zealand Patent Application No. 709729.
Judson et al., U.S. Appl. No. 29/258,083, filed Apr. 2006.
Judson et al., U.S. Appl. No. 29/258,085, filed Apr. 2006.
Jun. 24, 2015 Deadline for Counterstatement issued in corresponding New Zealand Patent Application No. 611284.
Mar. 25, 2013 Amended Notice of Opposition to Grant of Patent issued in New Zealand Application No. 590211.
Mar. 25, 2013 Statement of Case issued in New Zealand Application No. 590211.
May 27, 2016 Statement of Case filed in New Zealand Patent Application No. 709729 (12 pages).
Nov. 18, 2016 Amended Statement of Case filed in New Zealand Patent Application No. 709729 (28 pages).
Oct. 18, 2016 Amended Notice of Opposition to Grant of Patent issued in New Zealand Application No. 709729.
Oct. 29, 2012 Notice of Opposition issued in New Zealand Application No. 590211.
Sep. 25, 2015 Notice of Allowance issued in U.S. Appl. No. 12/312,308.
Dec. 21, 2017 Letter to IPONZ filed in New Zealand Patent Application No. 611284.
Jan. 7, 2019 Further Examination Report issued in New Zealand Patent Application No. 731139.
Nov. 30, 2018 Letter to IPONZ filed in New Zealand Patent Application No. 709729.
Nov. 30, 2018 Third Amended Notice of Opposition (marked up and clean formats) filed in New Zealand Patent Application No. 709729.
Nov. 30, 2018 Fourth Amended Statement of Case (marked up and clean formats) filed in New Zealand Patent Application No. 709729.

FRAME AND VENT ASSEMBLY FOR MASK ASSEMBLY

CROSS-REFERENCE TO APPLICATIONS

This application is a division of U.S. application Ser. No. 12/312,308, filed May 5, 2009, which is the U.S. national phase of International Application No. PCT/AU2007/001749, filed Nov. 14, 2007, which designated the U.S. and claims the benefit of U.S. Provisional Application No. 60/858,700, filed Nov. 14, 2006, each of which is incorporated herein by reference in its entirety.

FIELD OF THE INVENTION

The present invention relates to a frame and vent assembly for a mask assembly used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE INVENTION

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A washout vent in the mask or conduit discharges the exhaled gas from the mask to atmosphere.

The washout vent is normally located in the mask or near the mask in the gas delivery conduit coupled to the mask. The washout of gas through the vent to the atmosphere removes exhaled gases to prevent carbon dioxide build-up, and hence "rebreathing", which represent a health risk to the mask wearer. Adequate gas washout is achieved by selecting a vent size and configuration that allows a minimum safe washout flow at a low operating CPAP pressure, which typically can be as low as 4 cm $H_2O$ for adults and 2 cm $H_2O$ for children.

Noise is a significant issue in CPAP treatment for the patient and/or the patient's bed partner. Excessive noise can lead to patients being non-compliant with the CPAP therapy. One source of noise is the exhaust through the vent in the mask or conduit. The flow of gas through the vent creates noise as it exits to and interacts with the atmosphere. Noise can adversely affect patient and bed-partner comfort, depending on both the magnitude and character of the noise. Further, bi-level gas delivery regimes tend to generate more noise than do constant level gas delivery regimes. This is thought to be due to the extra turbulence created by the gas accelerating and decelerating as it cycles between relatively low and relatively high pressures in the bi-level gas delivery systems.

There is a long felt and continuing need to reduce the noise associated with the washout or venting of exhaled gases. Reducing the noise of gas being exhausted from a mask or conduit can significantly improve the user friendliness of the CPAP treatment.

SUMMARY OF THE INVENTION

One aspect of the invention relates to a nasal or full-face mask frame including a main body and a vent assembly provided to the main body. The vent assembly includes a plurality of holes arranged in at least one column. The holes are positioned on a relatively flat and/or non-recessed portion of the main body.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-7 are various views of an extra-small size frame for a full facial mask assembly according to an embodiment of the present invention;

FIG. 2-8 is a cross-sectional view of a frame according to an embodiment of the present invention;

FIG. 2-9 is an enlarged cross-section view of a vent hole according to an embodiment of the present invention;

FIG. 2-10 is an enlarged plan view of a relatively flat portion of a frame and vent assembly according to an embodiment of the present invention;

FIGS. 3-1 to 3-7 are various views of a small size frame for a full facial mask assembly according to an embodiment of the present invention;

FIGS. 4-1 to 4-7 are various views of a medium size frame for a full facial mask assembly according to an embodiment of the present invention; and FIGS. 5-1 to 5-7 are various views of a large size frame for a full facial mask assembly according to an embodiment of the present invention.

DETAILED DESCRIPTION OF ILLUSTRATED EMBODIMENTS

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Mask Assembly

Figure 1:
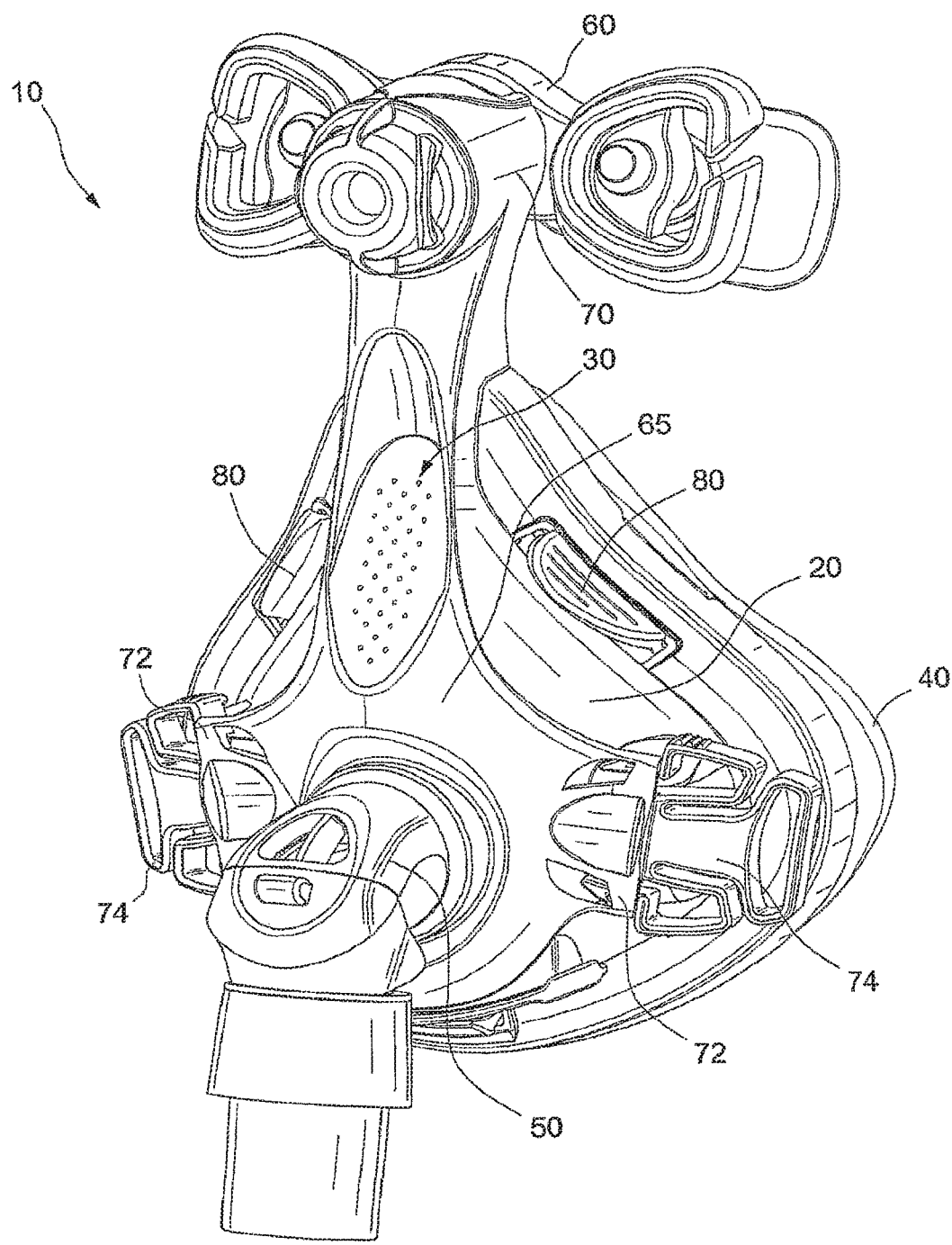
FIG. 1 is a front perspective view of a full facial mask assembly according to an embodiment of the present invention.
Figures 1, 2:
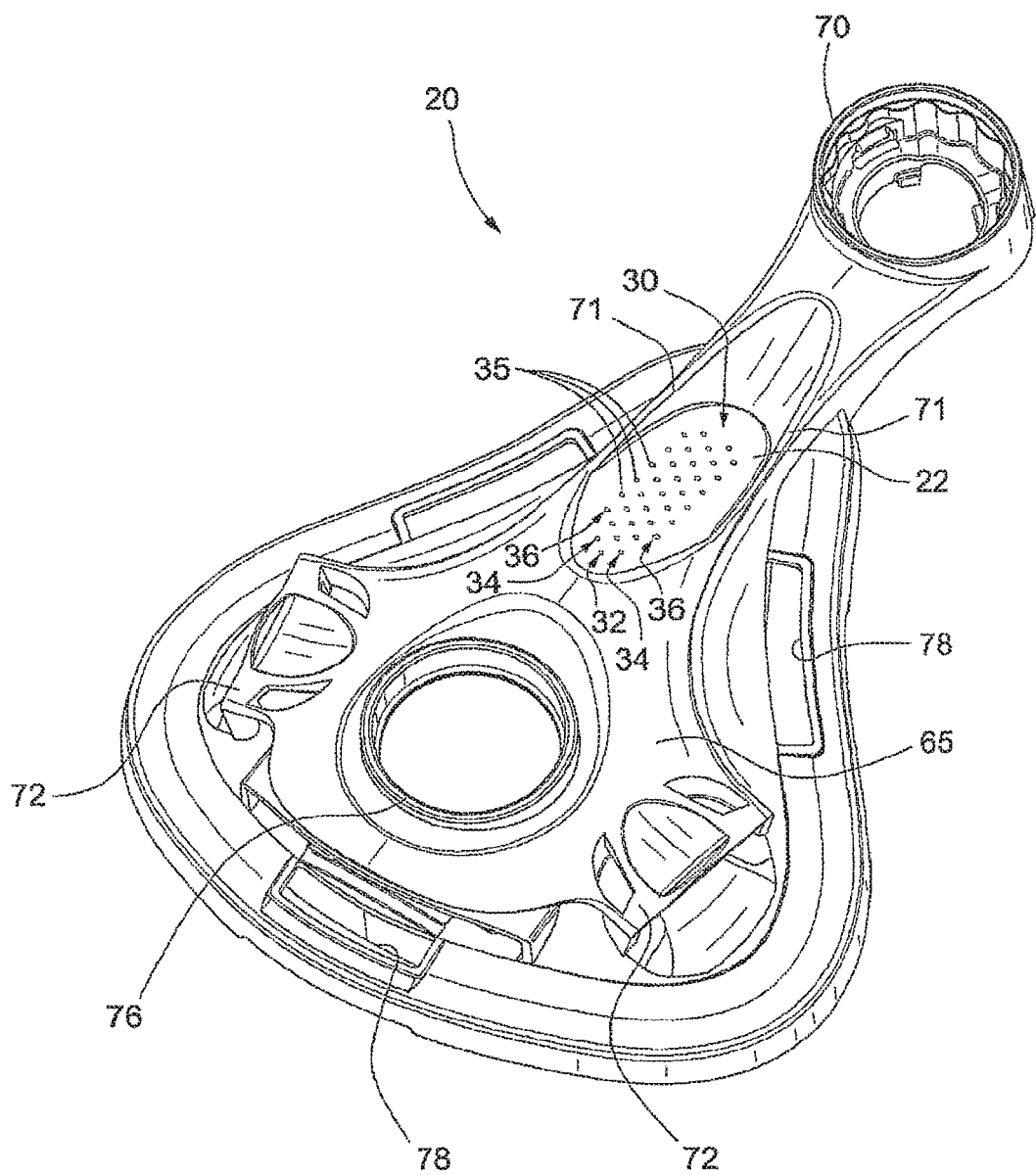
Figure 2:
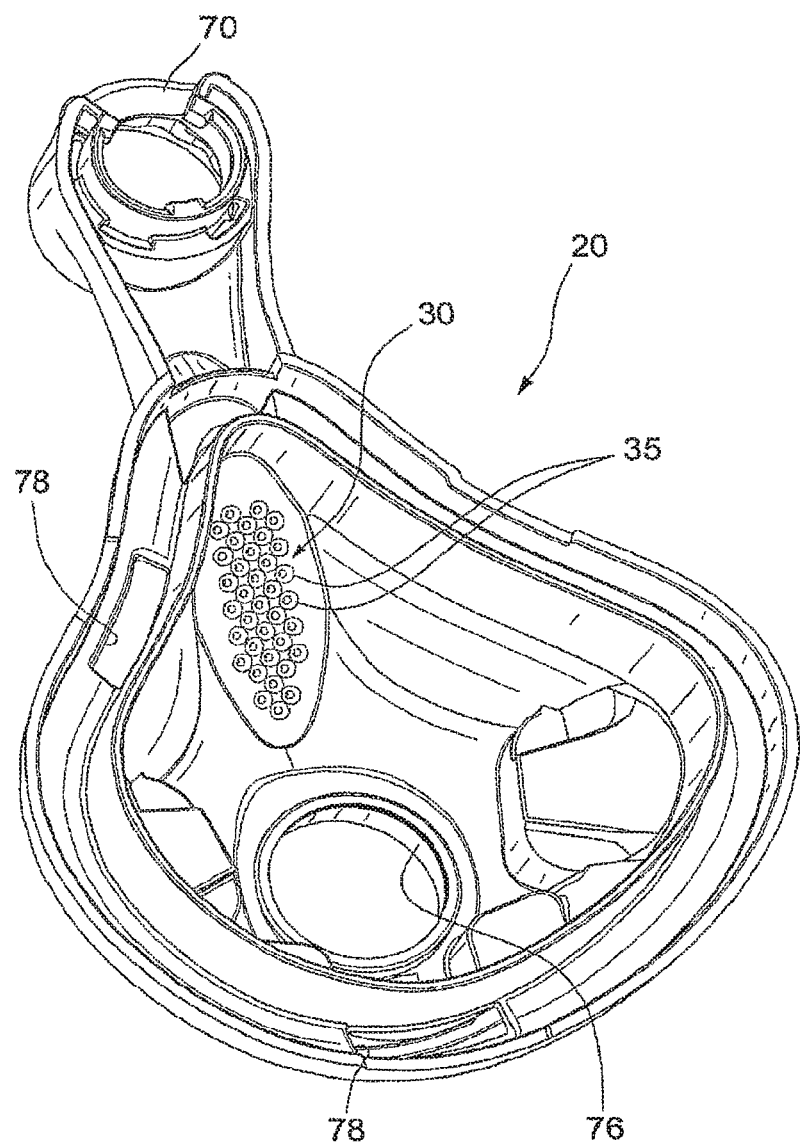
Figures 2, 3:
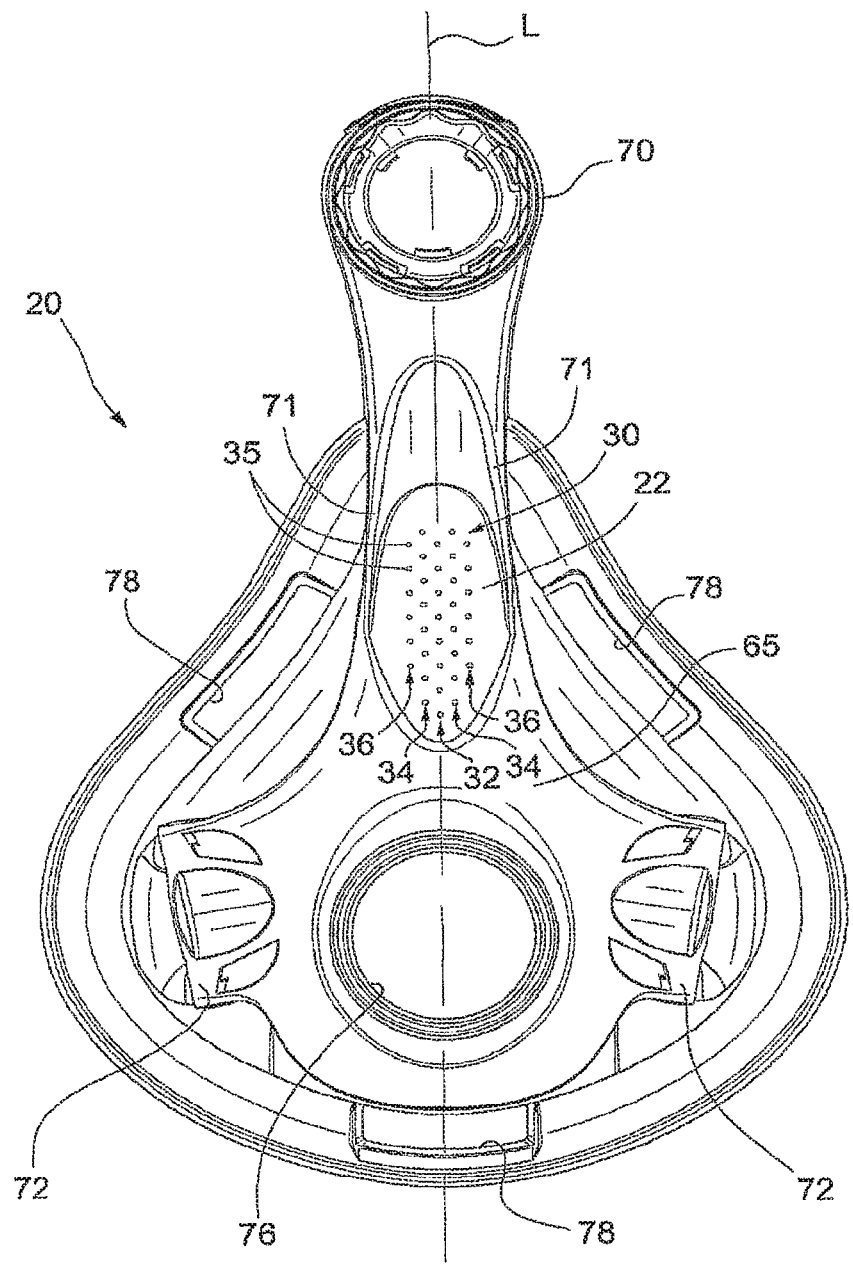
Figures 2, 3, 4:
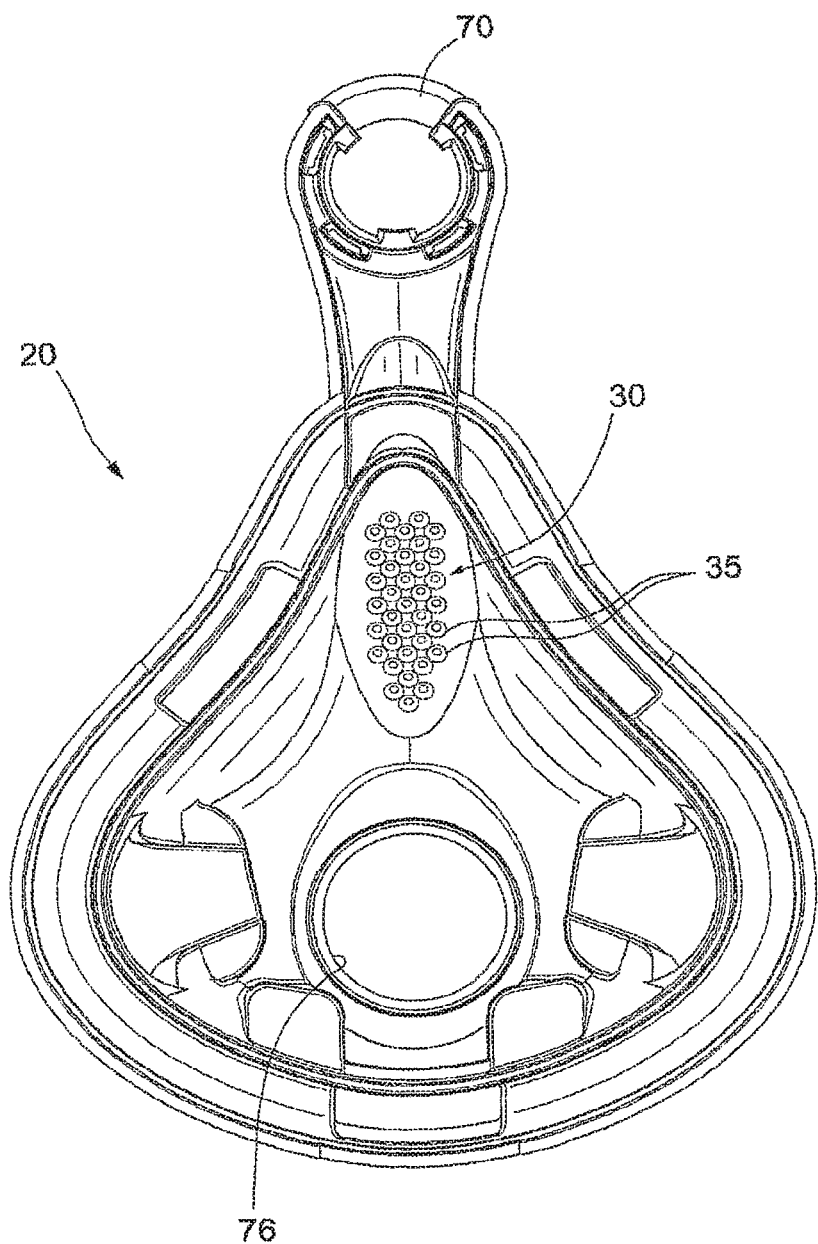
Figures 2, 3, 4, 5:
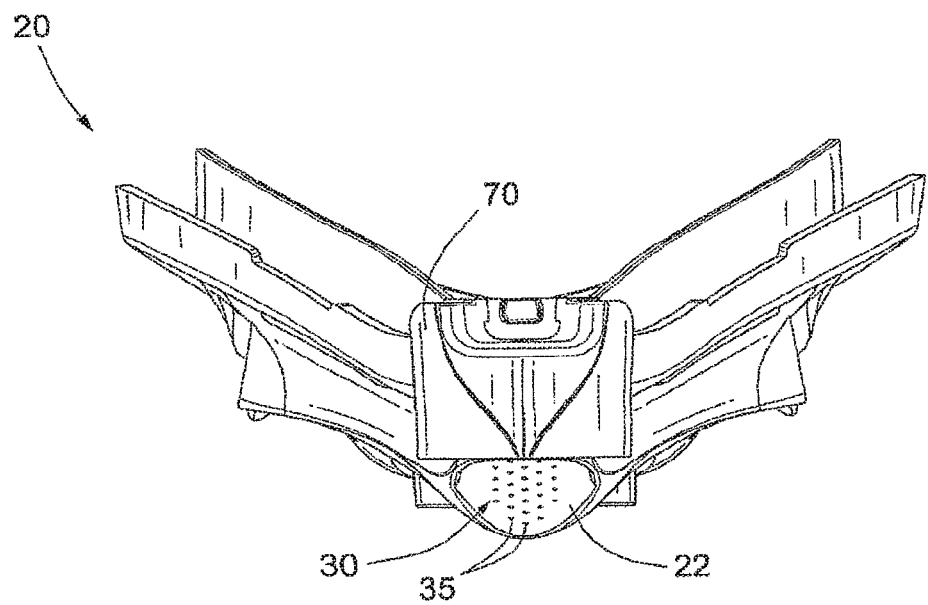
Figures 2, 3, 4, 5, 6:
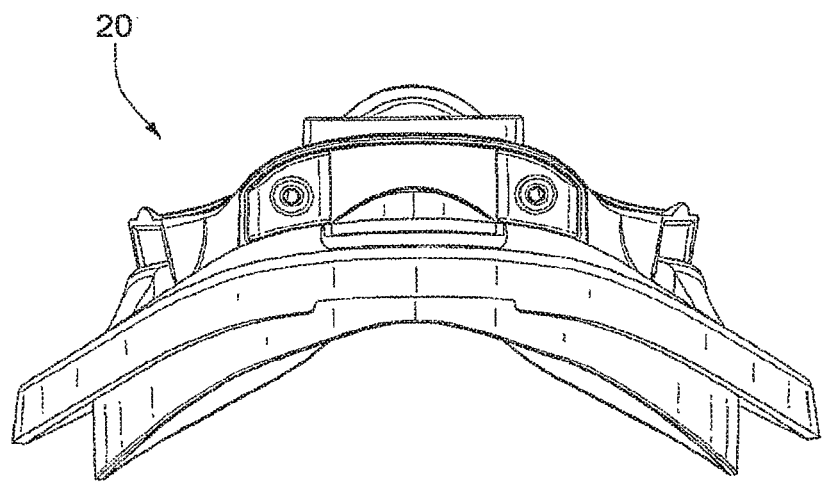
Figures 2, 3, 4, 5, 6, 7:
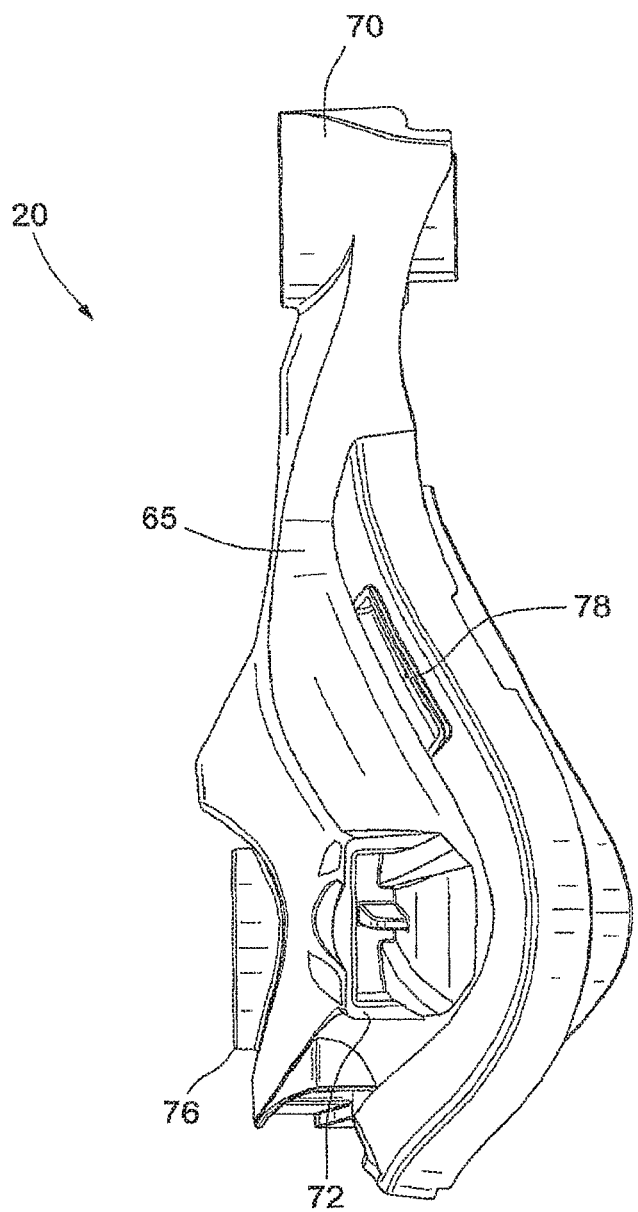
Figures 2, 3, 4, 5, 6, 7, 8:
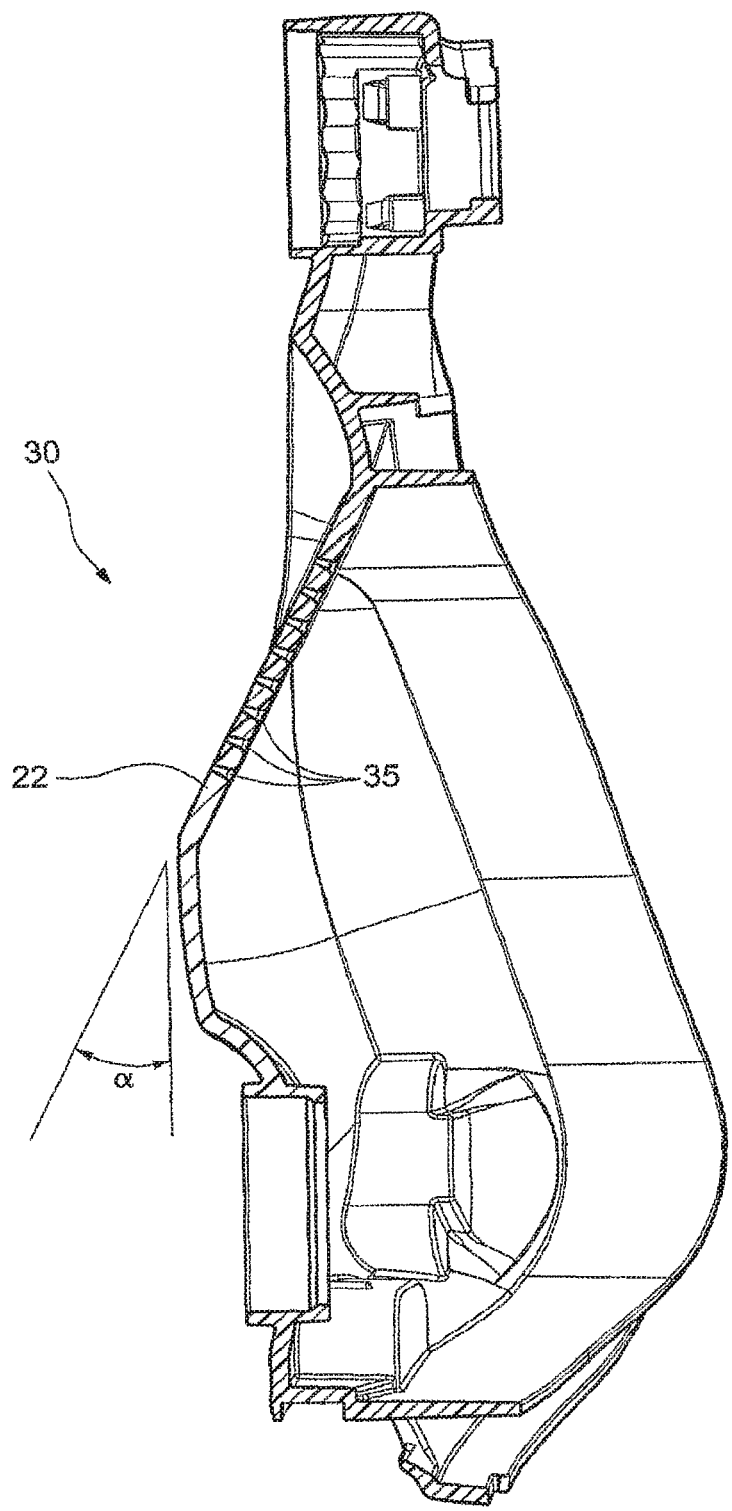
Figures 2, 3, 4, 5, 6, 7, 8, 9:
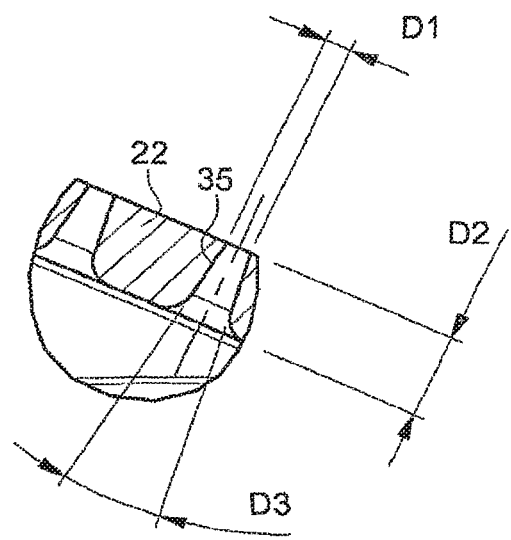
Figures 2, 3, 4, 5, 6, 7, 8, 9, 10:
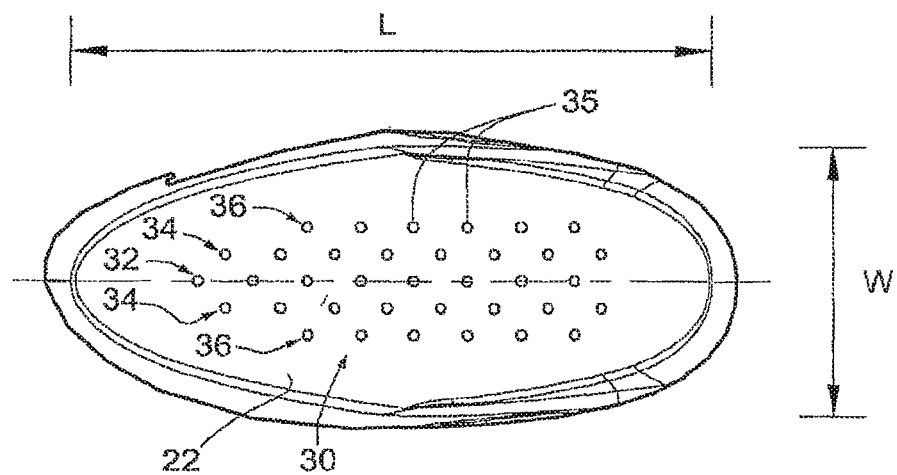
Figures 1, 3:
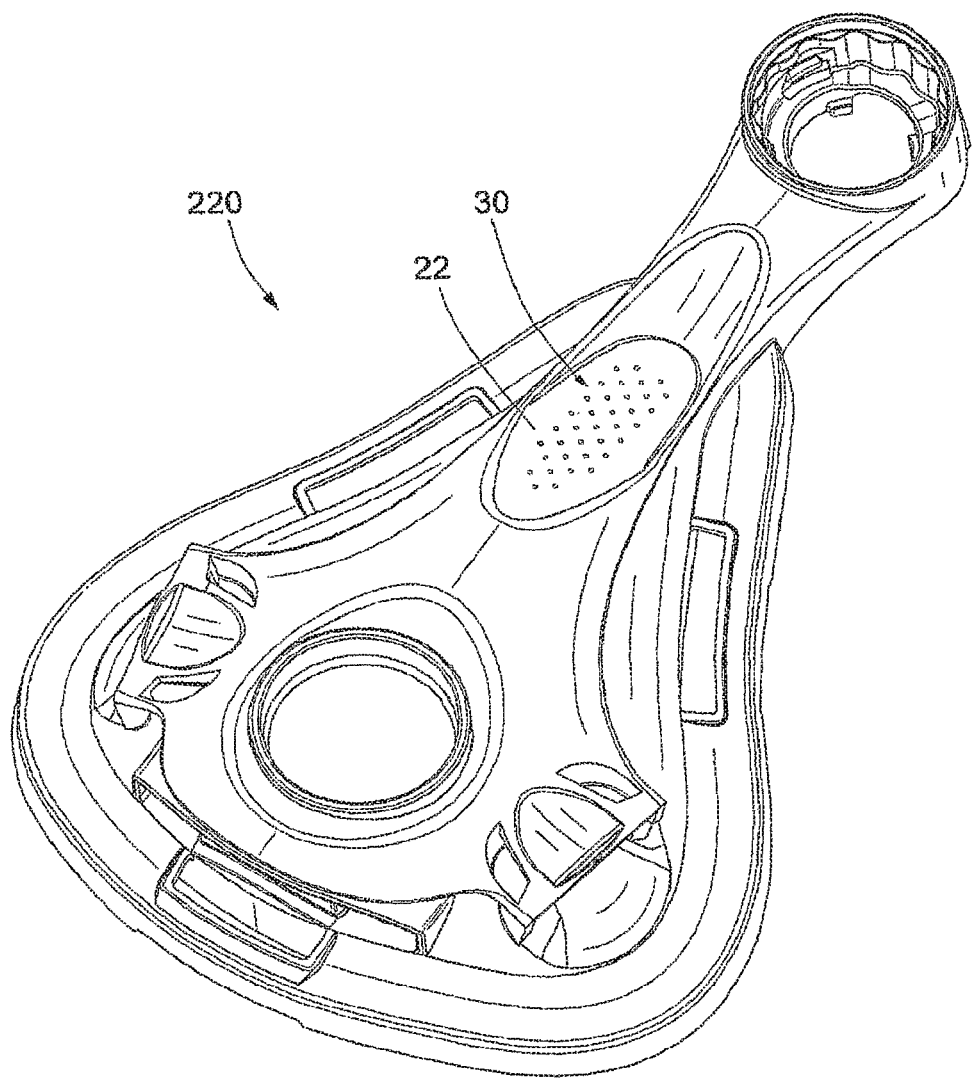
Figures 2, 3:
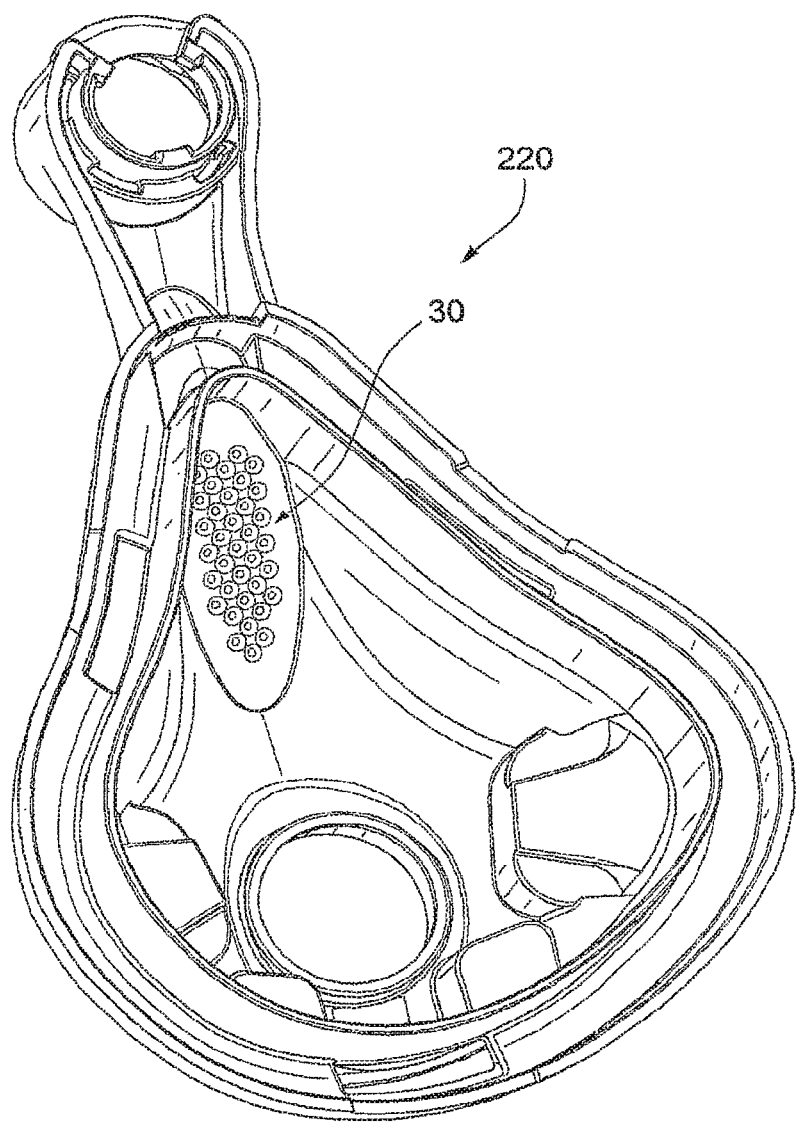
Figure 3:
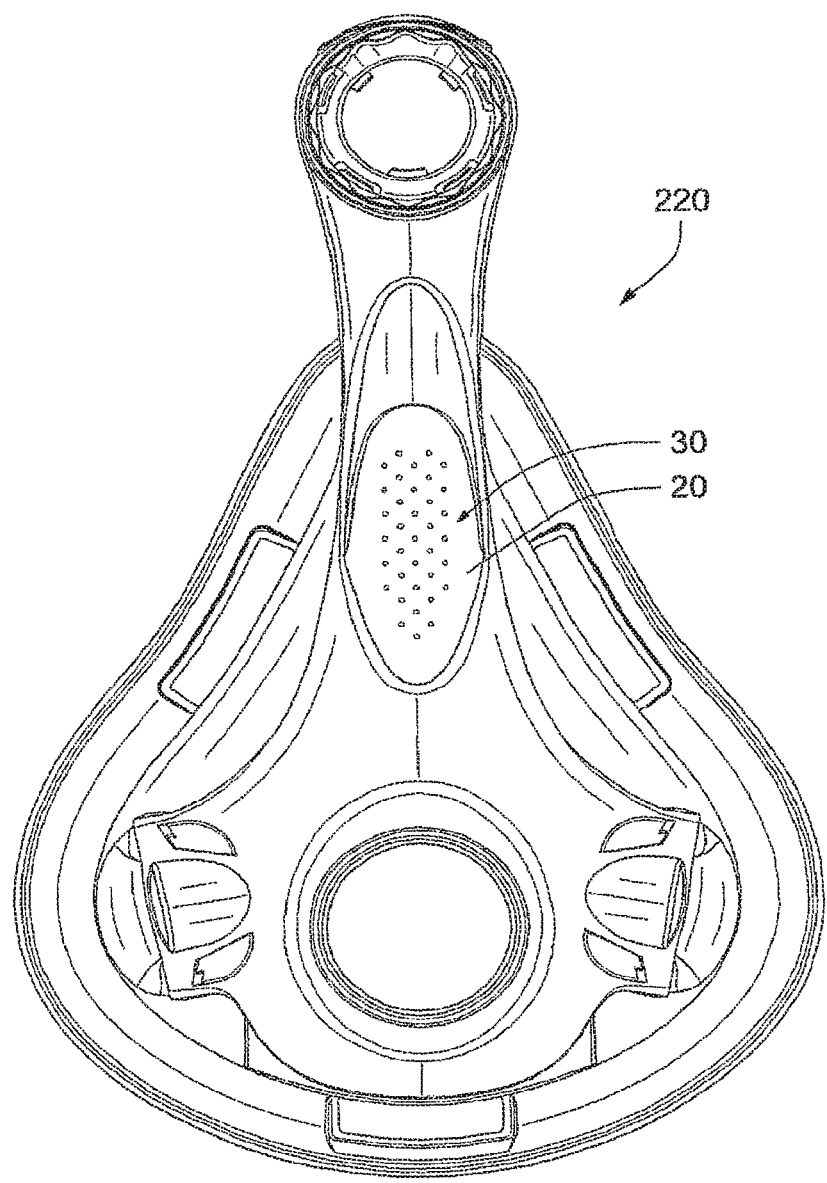
Figures 3, 4:
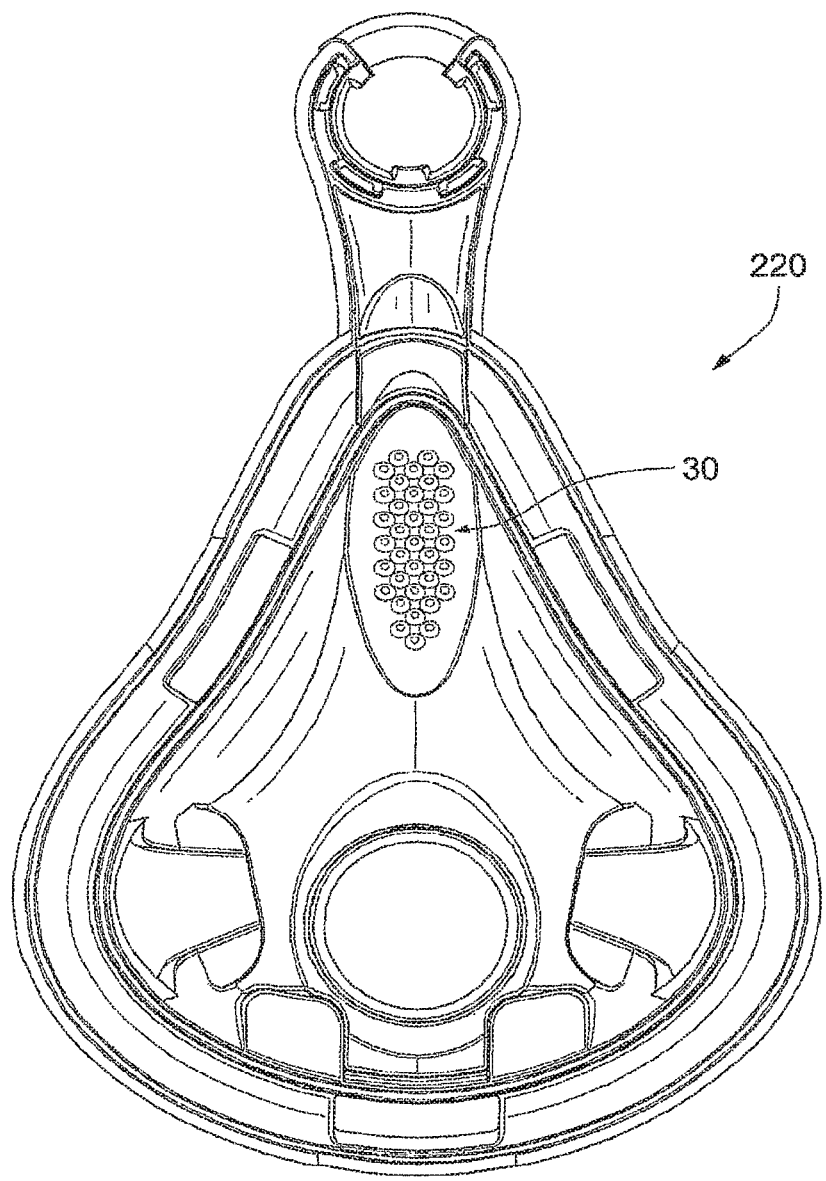
Figures 3, 4, 5:
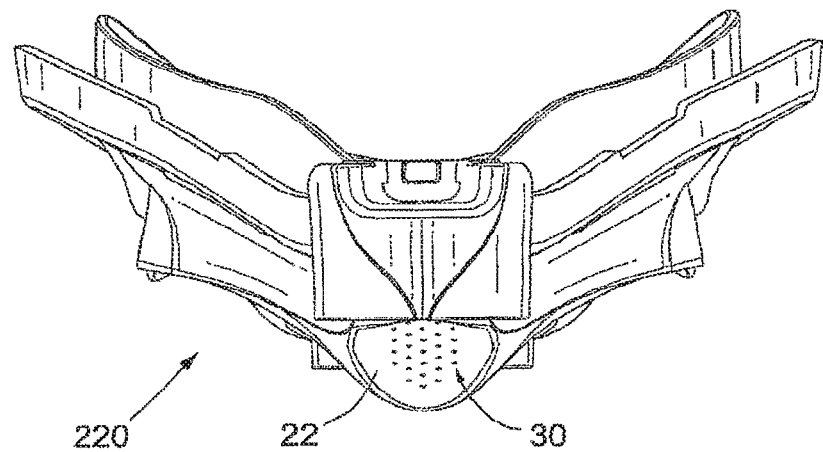
Figures 3, 4, 5, 6:
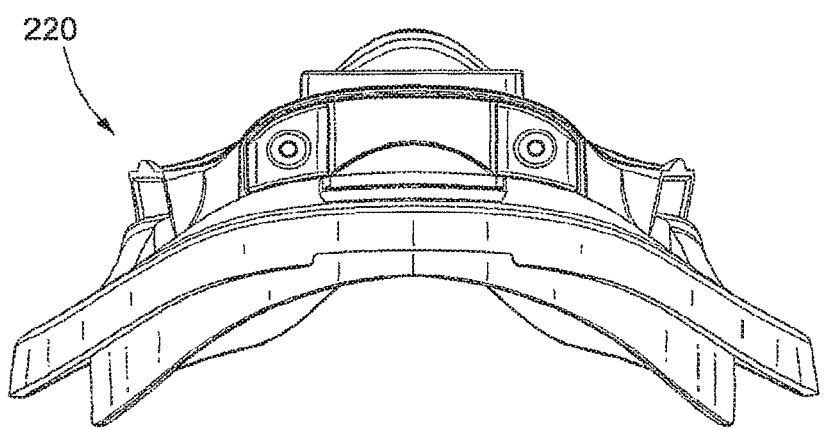
Figures 3, 4, 5, 6, 7:
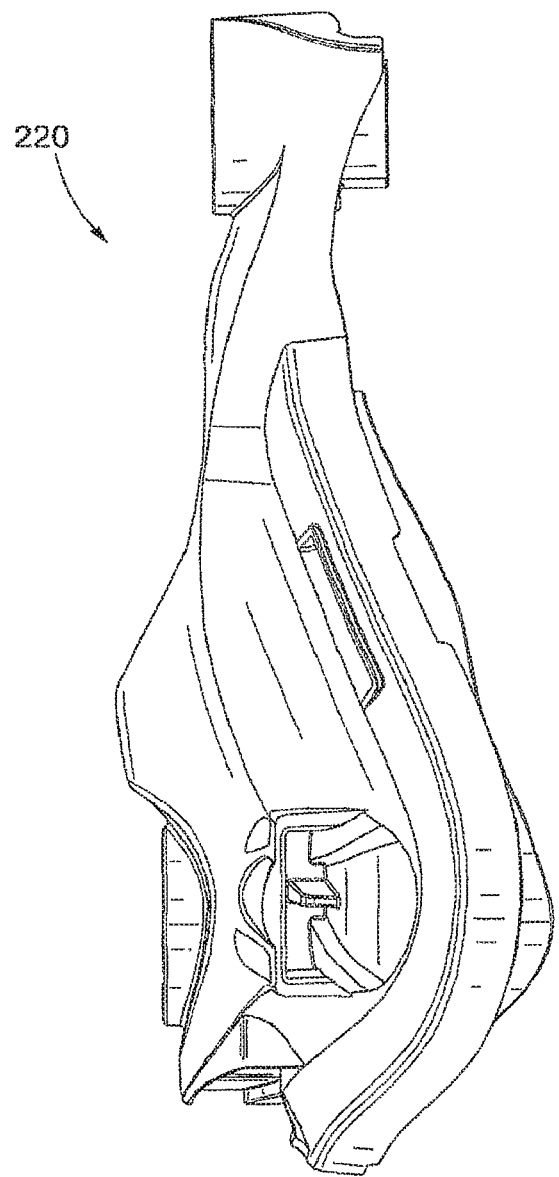
Figures 1, 4:
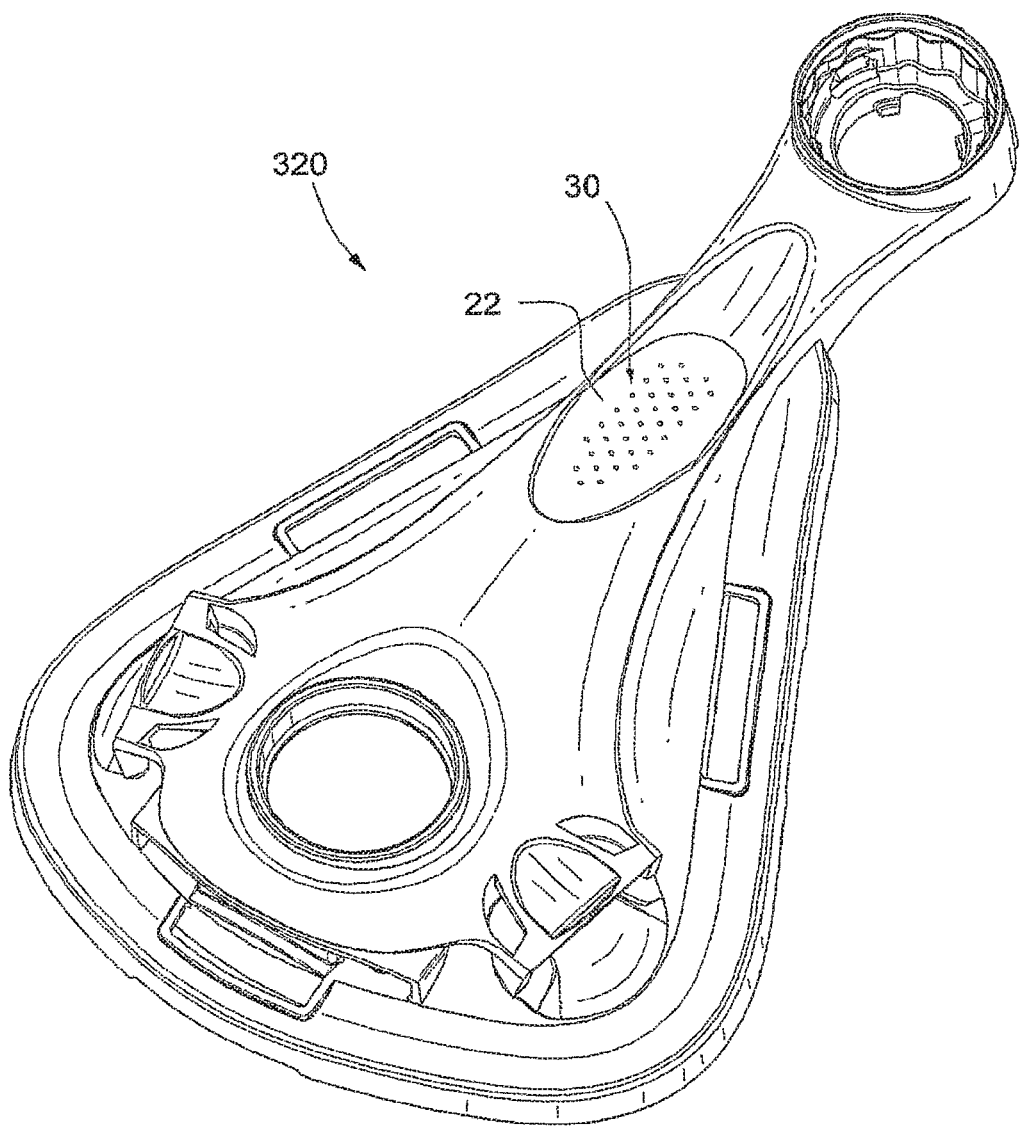
Figures 2, 4:
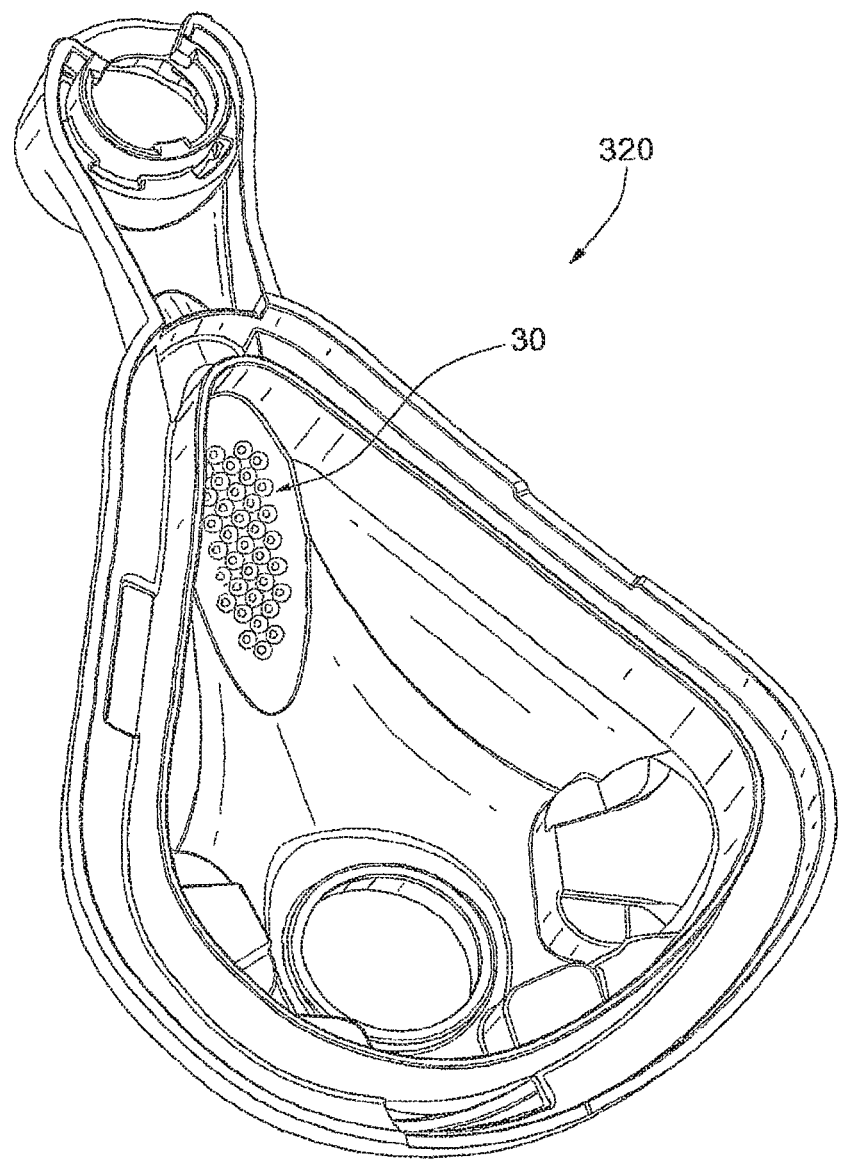
Figures 3, 4:
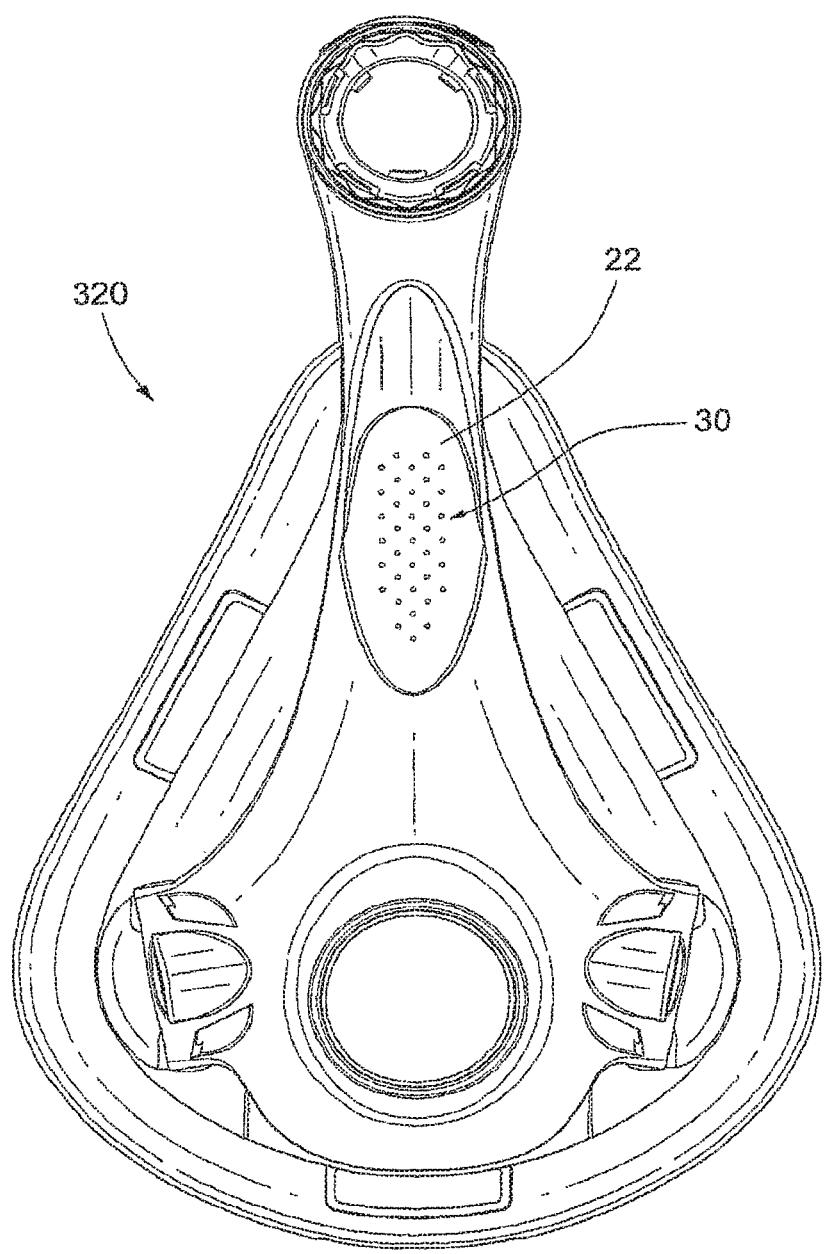
Figure 4:
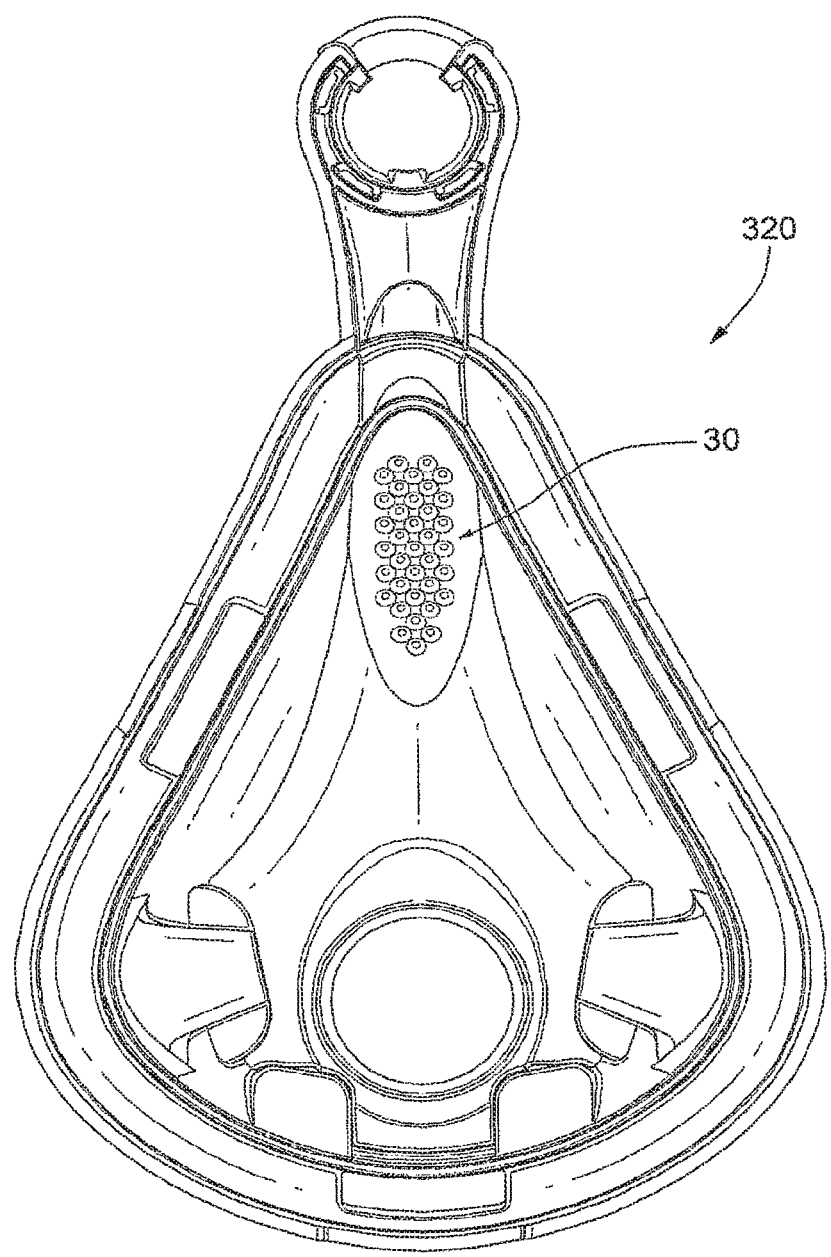
Figures 4, 5:
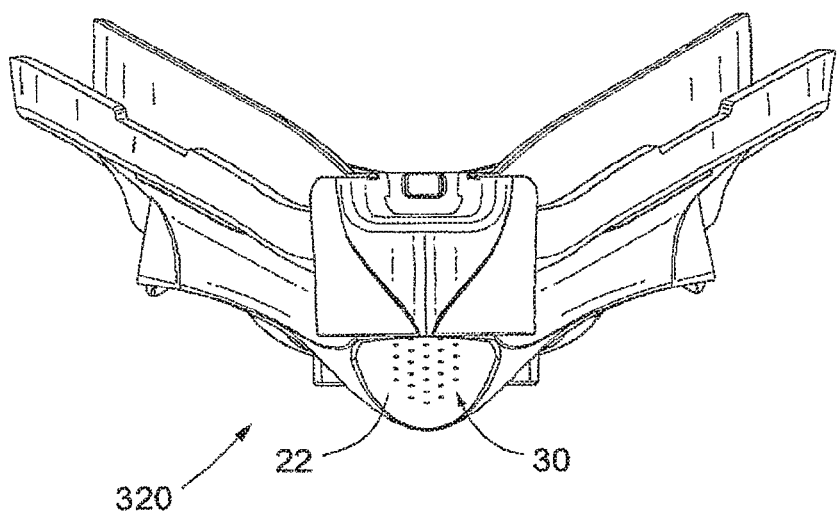
Figures 4, 5, 6:
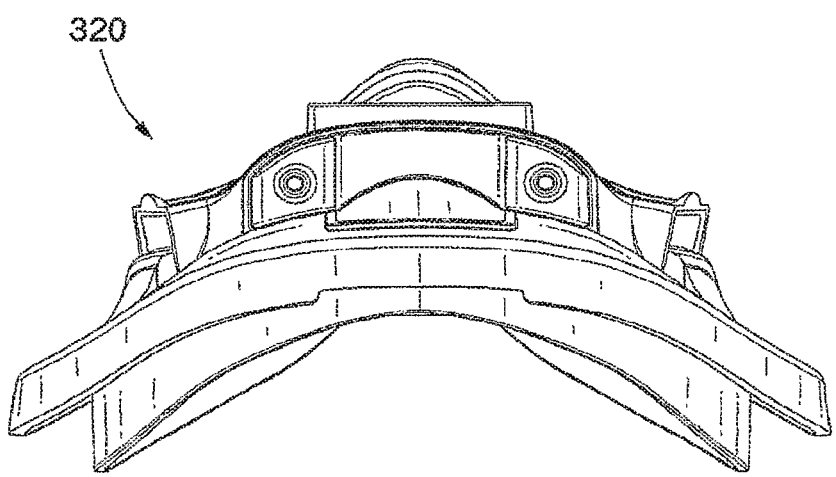
Figures 4, 5, 6, 7:
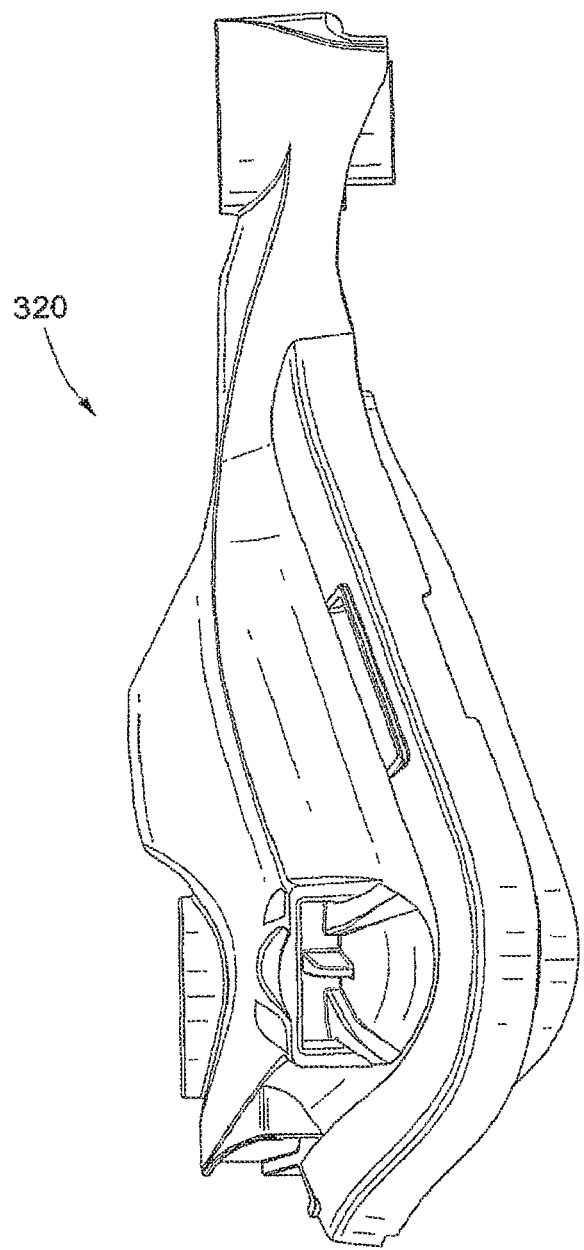
Figures 1, 5:
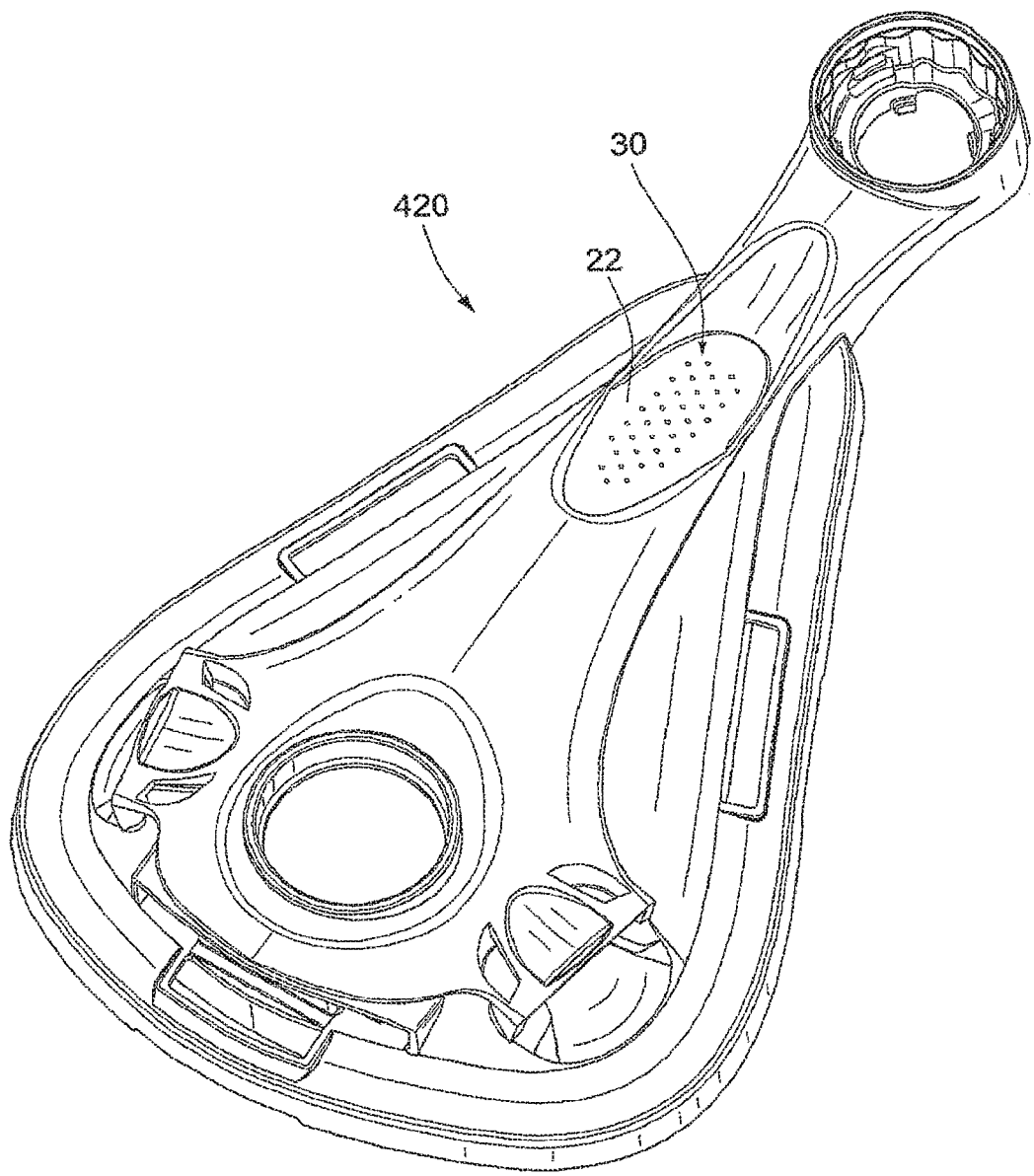
Figures 2, 5:
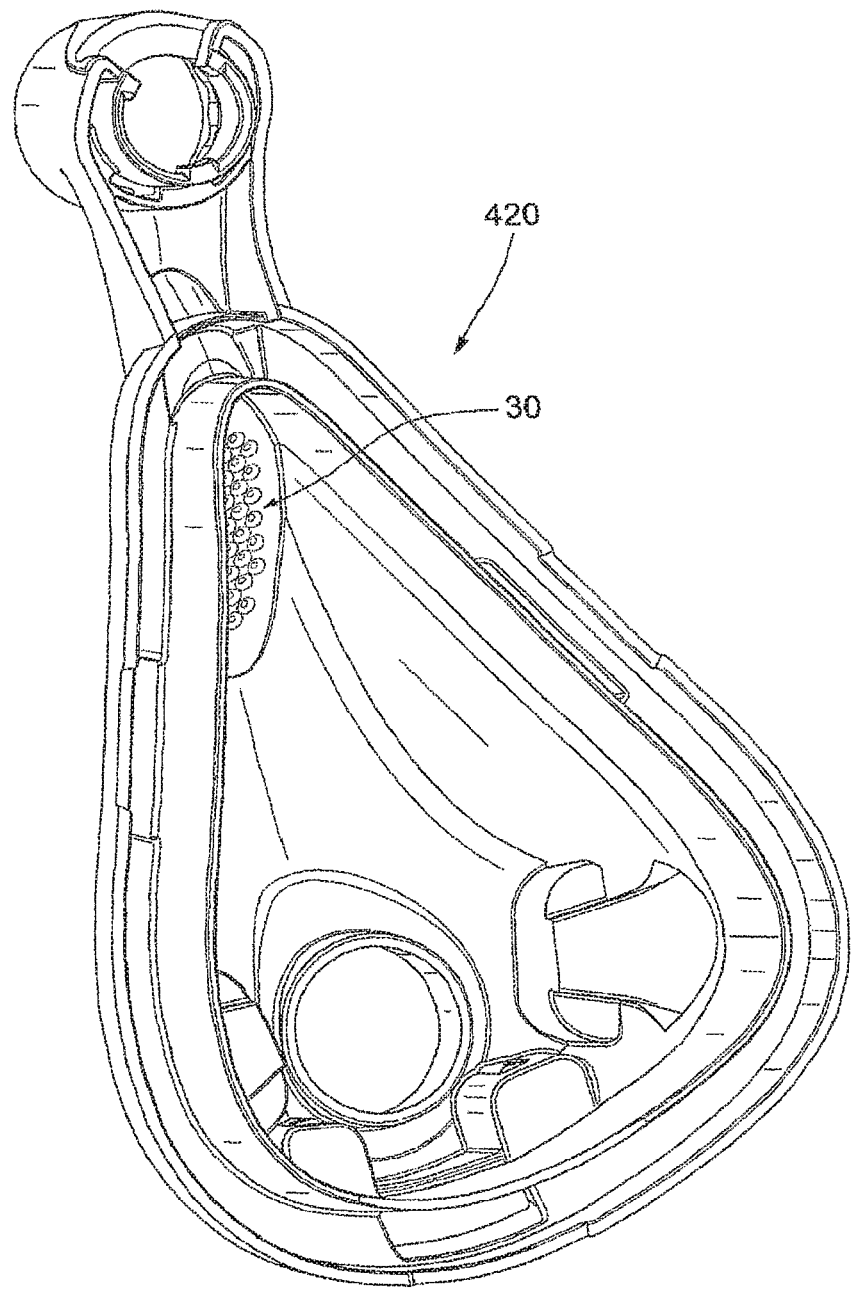
Figures 3, 5:
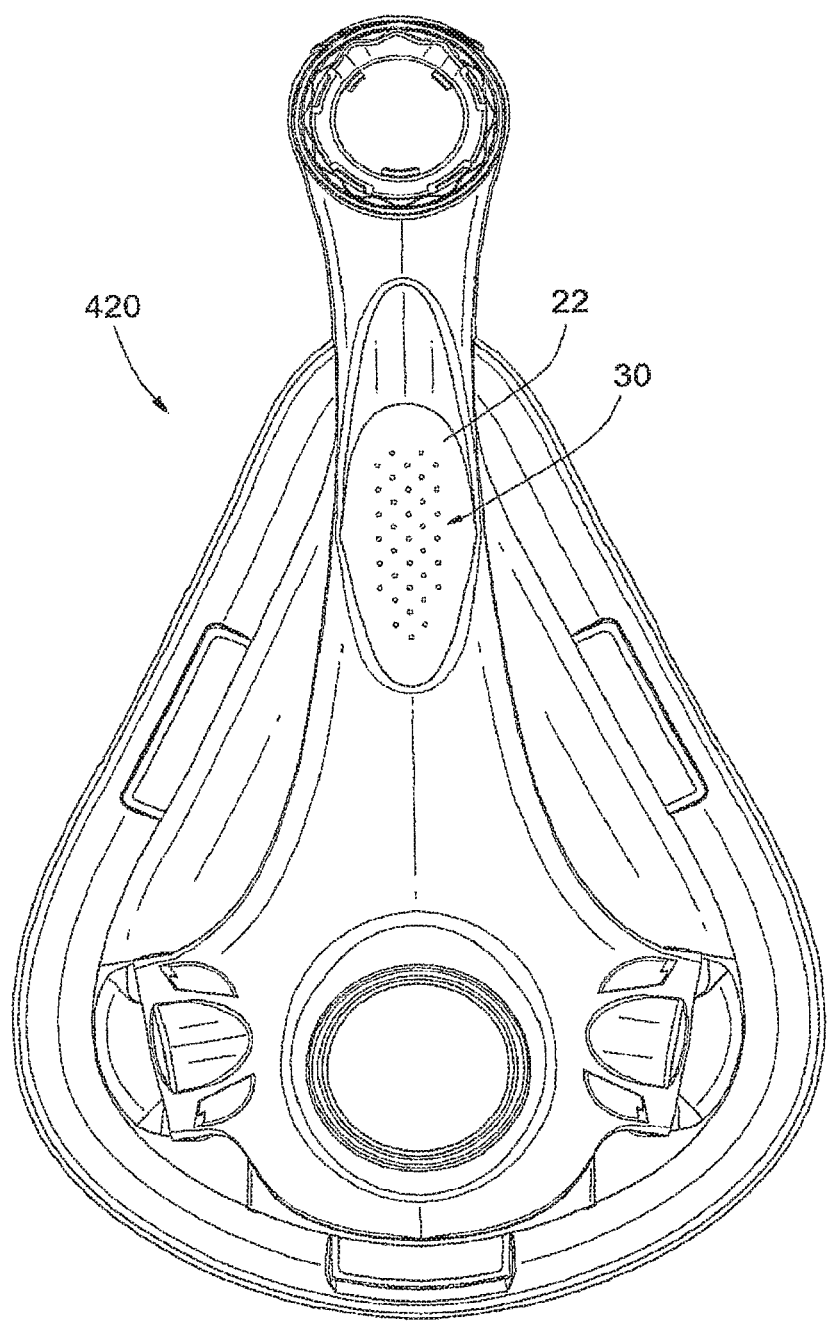
Figures 4, 5:
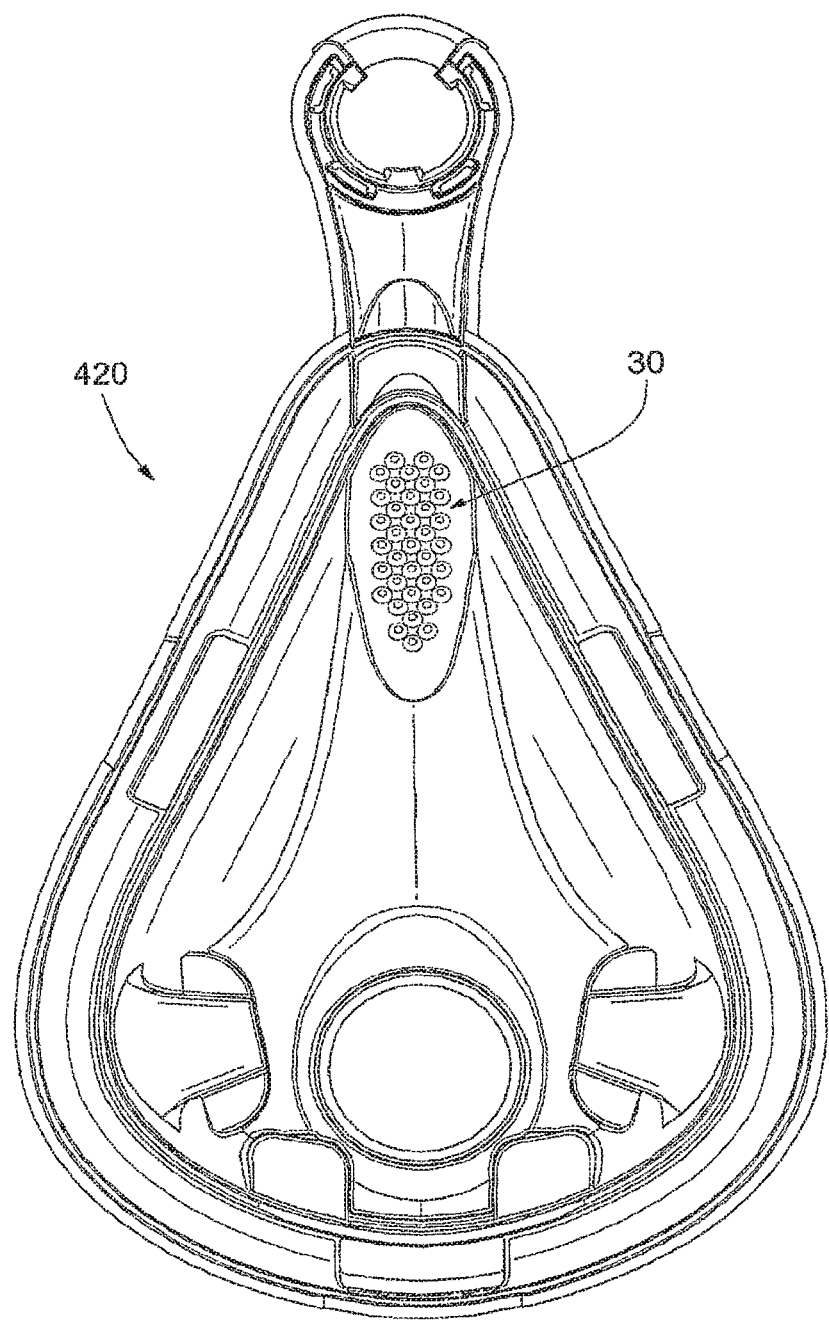
Figure 5:
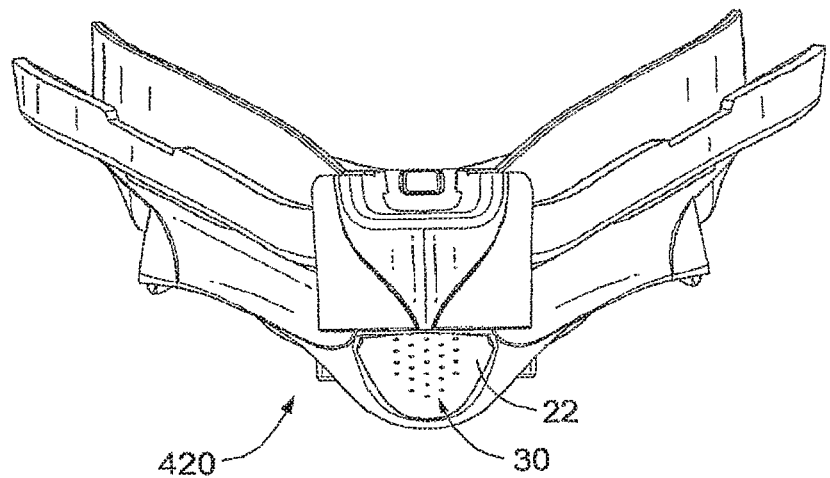
Figures 5, 6:
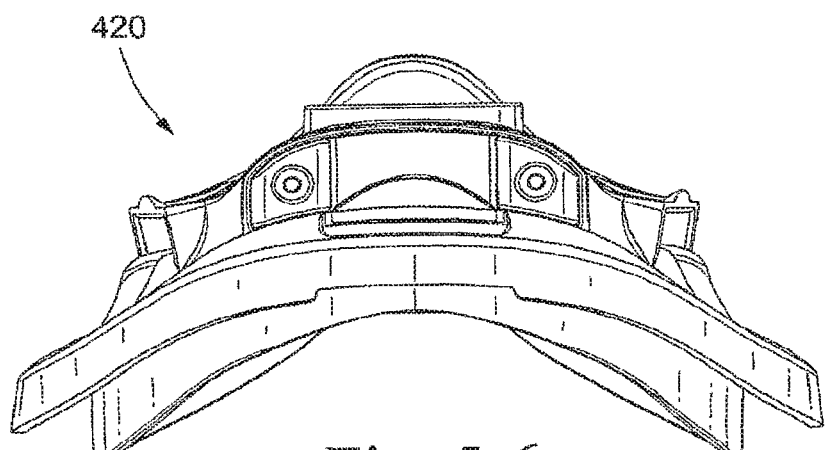
Figures 5, 6, 7:
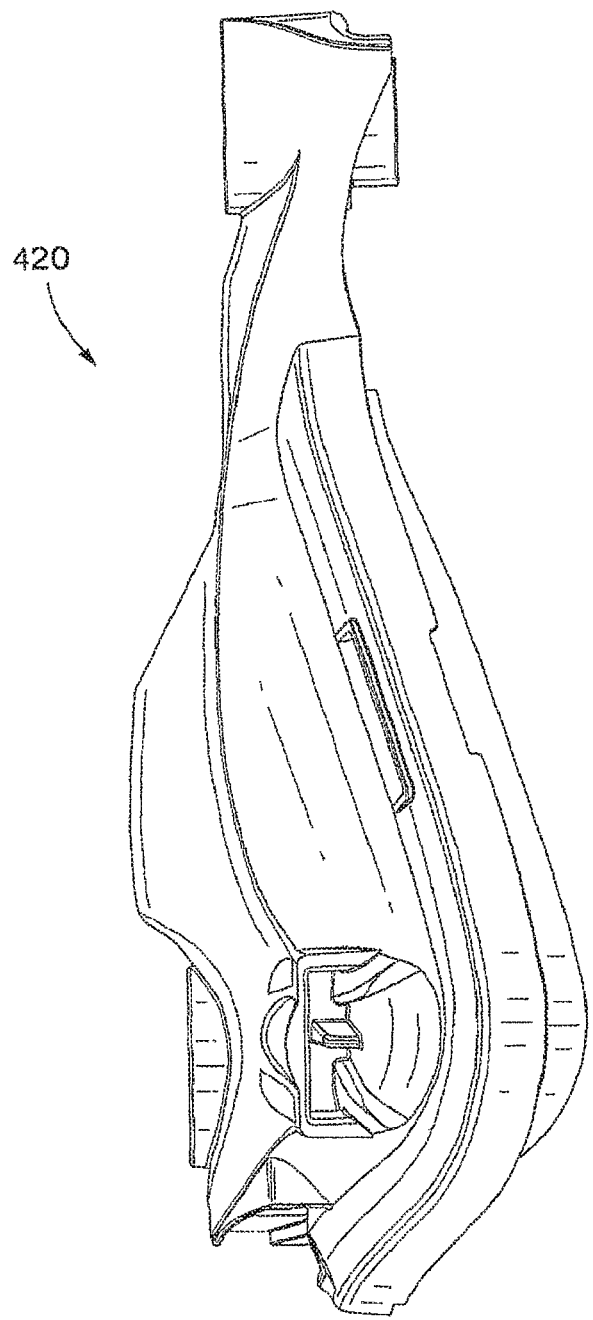

FIG. 1 illustrates an embodiment of a full facial mask assembly ("FMA") 10 including a frame 20 and vent assembly 30 according to an embodiment of the present invention. As illustrated, the mask assembly 10 includes a frame 20, a cushion 40 provided to the frame 20 and adapted to form a seal with the patient's face, an elbow assembly 50 provided to the frame 20 and adapted to be connected to an air delivery tube (not shown) that delivers breathable gas to the patient, and a forehead support 60 to provide a support and stability mechanism between the mask assembly 10 and the patient's forehead. A headgear assembly (not shown) may be removably attached to the frame 20 and the forehead support 60 to maintain the mask assembly 10 in a desired adjusted position on the patient's face.

Further details and embodiments of this type of mask assembly are disclosed in PCT Application Nos. PCT/

AU2006/000031, PCT/AU2006/000035, and PCT/AU2006/000037, each of which is incorporated herein by reference in its entirety.

Mask Frame

FIGS. 2-1 to 2-7 illustrate the frame 20 isolated from the other components of the mask assembly 10. As illustrated, the frame 20 includes a main body 65, an upper support member 70 adapted to support the forehead support 60, lower headgear clip receptacles 72 adapted to be engaged with clips 74 (e.g., see FIG. 1) provided to straps of a headgear assembly (not shown), and a lower bore or annular elbow connection seal 76 adapted to engage the elbow assembly 50. Also, the top wall of the frame 20 includes a plurality of slots 78 therethrough, e.g., three slots, that are adapted to engage a cushion clip 80 (portions of clip 80 shown in FIG. 1) that retains the cushion 40 to the frame 20. In addition, the frame 20 includes a vent assembly 30 for gas washout. In an embodiment, the frame 20 is molded in one-piece with polycarbonate.

Vent Assembly

As best shown in FIGS. 2-1 to 2-5, 2-8, and 2-10, the vent assembly 30 is provided to an upper portion of the frame 20. Specifically, the vent assembly 30 is positioned on a relatively flat portion 22 of the frame 20 between spaced-apart side walls 71 of the upper support member 70. As illustrated, the relatively flat portion 22 has a generally oval shape and defines a relatively smooth, planar surface. Moreover, the relatively flat portion 22 is not substantially recessed with respect to the surrounding portions of the frame 20, e.g., not concave.

In an embodiment, as best shown in FIG. 2-10, the relatively flat portion 22 may have a length L of about 40-50 mm, e.g., 44.72 mm, and a width W of about 15-20 mm, e.g., 18 mm. In addition, the relatively flat portion 22 may be inclined with respect to vertical to direct exhausted air upwardly and outwardly from the flame in use. In an embodiment, as best shown in FIG. 2-8, the relatively flat portion 22 may be inclined at an angle α with respect to vertical. The angle α may be about 20°-30°, e.g., 25°. Although specific dimensions and ranges of the relatively flat portion 22 are indicated, it is to be understood that these dimensions and ranges are merely exemplary and other dimensions and ranges are possible depending on application. For example, the exemplary dimensions may vary by 10-20% or more or less depending on application.

This arrangement allows gas to freely exit the vent assembly 30, which results in less noise. Specifically, the vent assembly 30 is positioned on the relatively flat portion 22 so that gas exiting the vent assembly 30 will have less interference with the frame 20. Less gas interference with the frame 20 results in less noise.

In the illustrated embodiment, the vent assembly 30 includes a plurality of holes 35 arranged in a five column pattern. The five column pattern includes a center column 32, flanked by intermediate columns 34, which in turn are flanked by outside columns 36. As illustrated, the columns 32, 34, 36 are aligned or parallel to the longitudinal axis L of the frame 20, e.g., the center column 32 is aligned with the longitudinal axis L and the intermediate and outside columns 34, 36 are parallel to the longitudinal axis L (see FIG. 2-3).

The center column 32 includes 3-20 holes, e.g., 8 holes, the intermediate columns 34 each include 3-20 holes, e.g., 8 holes, and the outside columns 36 each include 3-20 holes, e.g., 6 holes. As illustrated, the holes in the center column 32 are offset with the holes in the intermediate columns 34. Also, the holes in the center column 32 are aligned with the holes in the outside columns 36, with the center column 32 having two additional holes at the lower end.

In the illustrated embodiment, each hole 35 has a generally part conic shape, including opposed walls that converge from a larger (inside) diameter to a smaller (outside) diameter, as viewed in the direction of exhausted gas. In an embodiment, as best shown in FIG. 2-9, D1 may be about 0.65-0.75 mm, e.g., 0.7 mm, D2 may be about 2-3 mm, e.g., 2.4 mm, and D3 may be about 13.5°-14.5°, e.g., 14°. Although specific dimensions and ranges of the hole are indicated, it is to be understood that these dimensions and ranges are merely exemplary and other dimensions and ranges are possible depending on application. For example, the exemplary dimensions may vary by 10-20% or more or less depending on application.

As illustrated, all the holes 35 are positioned within the flat portion 22. The holes are positioned relatively compact such that the holes are nearly touching when viewed from an inner side of the frame (e.g., see FIGS. 2-2 and 2-4). The holes and/or hole arrangement may be designed to reduce noise.

However, the frame 20 may include other suitable vent arrangements. For example, the frame 20 may include vent arrangements such as those described in U.S. Patent Publication No. WO 2006/074516, published Jul. 20, 2006, and PCT Application No. PCT/AU20061001507, filed Oct. 13, 2006, which claims the benefit of U.S. Design application Ser. No. 29/258,084, filed Apr. 14, 2006, and U.S. Provisional Patent Application Nos. 60/734,282, filed Nov. 8, 2005, 60/758,200, filed Jan. 12, 2006, 60/795,615, filed Apr. 28, 2006, 60/819,626, filed Jul. 11, 2006, and 60/838,442, filed Aug. 18, 2006, each of which is incorporated herein by reference in its entirety. The vent arrangement is preferably incorporated into the flat portion 22 of the frame 20 so there is less gas interference with the frame 20.

Frame Size

The mask frame 20 may be provided in various sizes, e.g., extra-small, small, medium, and large, to accommodate a wide range of patients. For example, FIGS. 2-1 to 2-7 illustrate an extra-small size frame 20, FIGS. 3-1 to 3-7 illustrate a small size frame 220, FIGS. 4-1 to 4-7 illustrate a medium size frame 320, and FIGS. 5-1 to 5-7 illustrate a large size frame 420. The components of the various size frames 20, 220, 320, 420 are substantially similar and indicated with similar reference numerals. It should be appreciated that any suitable number of sizes may be provided.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed:

1. A mask frame for a mask assembly useful for treating sleep disordered breathing of a patient, the frame comprising: a one-piece main body of molded polycarbonate material; and a vent portion adapted to allow washout of gases exhaled by the patient, the vent portion being provided to the main body, the vent portion including a plurality of holes of substantially circular cross section arranged in the polycarbonate material, wherein all of the holes extend through the molded material and are positioned on a continuous, substantially planar portion of the main body, the substantially planar portion containing all of the holes being positioned and aligned between an apex of the main body and an aperture to receive an elbow, the aperture being positioned below the apex, the continuous, substantially planar portion containing all of the holes being laterally centered with respect to the apex, wherein at least a part of the substantially planar portion is not substantially recessed with respect to surrounding portions of the frame and the holes of the vent portion are grouped on the substantially planar portion, so that gas exiting the holes will avoid interference with the frame, thereby helping to reduce noise; and wherein the substantially planar portion is positioned on the main body at a location generally corresponding to a nasal bridge of a patient when the mask frame is positioned on a face of the patient.

2. The mask frame according to claim 1, further comprising an upper support member adapted to support a forehead support.

3. The mask frame according to claim 2, wherein the substantially planar portion is aligned between sides of the upper support member.

4. The mask frame according to claim 2, wherein the substantially planar portion is between spaced-apart side walls of the main body that are continuous with sides of the upper support member.

5. The mask frame according to claim 4, wherein the sides of the upper support member are integral with the main body of the mask frame.

6. The mask frame according to claim 4, wherein the substantially planar portion is at least partially defined by the spaced-apart side walls of the main body.

7. The mask frame according to claim 4, wherein the spaced-apart side walls extend beyond the main body of the mask frame.

8. The mask frame according to claim 1, wherein the substantially planar portion has a generally oval shape.

9. The mask frame according to claim 1, wherein the substantially planar portion defines a substantially smooth surface.

10. The mask frame according to claim 1, wherein a lowermost part of the substantially planar portion is not substantially recessed with respect to surrounding portions of the frame.

11. The mask frame according to claim 1, wherein the substantially planar portion is inclined with respect to vertical so that the holes are adapted to direct exhausted air upwardly and outwardly from the frame.

12. The mask frame according to claim 11, wherein the substantially planar portion is inclined about 20°-30° with respect to vertical.

13. The mask frame according to claim 12, wherein the substantially planar portion is inclined about 25° with respect to vertical.

14. The mask frame according to claim 1, wherein the substantially planar portion has a length of about 40-50 mm and a width of about 15-20 mm.

15. The mask frame according to claim 14, wherein the substantially planar portion has a length of about 44.72 mm and a width of about 18 mm.

16. The mask frame according to claim 1, wherein the main body has a vertical longitudinal axis and the holes are arranged in at least one vertical column aligned with or parallel to the longitudinal axis.

17. The mask frame according to claim 1, wherein each hole has a generally part conic shape including opposed walls that converge from a larger diameter to a smaller diameter as viewed in the direction of exhausted gas.

18. The mask frame according to claim 17, wherein each hole has a smaller diameter of about 0.65-0.75 mm, a length of about 2-3 mm, and a converge angle of about 13.5°-14.5°.

19. The mask frame according to claim 18, wherein each hole has a smaller diameter of about 0.7 mm, a length of about 2.4 mm, and a converge angle of about 14°.

20. The mask frame according to claim 1, further comprising lower headgear clip receptacles adapted to be engaged with clips provided to straps of a headgear assembly.

21. The mask frame according to claim 1, further comprising a plurality of slots adapted to engage a cushion clip that retains a cushion on the frame.

22. A mask assembly for treatment of obtrusive sleep apnea comprising: the mask frame according to claim 1; and a cushion attached to the mask frame, the cushion being made of a silicone material.

23. The mask frame according to claim 1, wherein the molded material comprises polycarbonate, and each of the holes extends through the polycarbonate.

24. The mask frame according to claim 1, wherein a substantially curved surface separates the aperture and the substantially planar portion.

25. The mask frame according to claim 24, wherein the substantially planar portion and the aperture are oriented in diverging directions.

26. The mask frame according to claim 1, wherein the mask frame is a full-face mask frame.

27. The mask frame of claim 1, wherein at least part of the substantially planar portion smoothly transitions to surrounding portions of the main body.

28. The mask assembly according to claim 1, wherein the substantially planar portion is flat.

29. The mask frame according to claim 1, wherein the plurality of holes includes at least six holes.

30. A mask frame for a mask assembly useful for treating sleep disordered breathing of a patient, the mask frame comprising: a one piece main body comprising molded polycarbonate material, said main body having a bore adapted to engage an elbow assembly, said main body defining a vertically oriented longitudinal axis extending across a center of the bore, said main body having a continuous vent surface intersecting the longitudinal axis as seen in front view and being positioned superior to the bore, the vent surface being substantially planar as seen in a cross-section taken perpendicular to the longitudinal axis; and a pattern of holes adapted to allow washout of gases exhaled by the patient, the pattern of holes being arranged in at least one substantially vertical column positioned on said continuous, substantially planar vent surface, said column extending substantially parallel to the longitudinal axis, all of said holes extending through the molded polycarbonate material and being positioned on the continuous, substantially planar vent surface, wherein at least a part of the substantially planar vent surface is not substantially recessed with respect to surrounding portions of the frame and the vent surface is positioned and oriented on the main body, so as to reduce noise-inducing interference between gas exiting the holes and adjacent portions of the main body.

31. The mask frame according to claim 30, further comprising an upper support member adapted to support a forehead support.

32. The mask frame according to claim 30, wherein the vent surface is inclined with respect to vertical so that the holes are adapted to direct exhausted air upwardly and outwardly from the frame.

33. The mask frame according to claim 30, wherein each hole converges from a larger diameter to a smaller diameter as viewed in the direction of exhausted gas.

34. The mask frame according to claim 30, further comprising lower headgear clip attachment points adapted to be engaged with clips provided to straps of a headgear assembly.

35. The mask frame according to claim 30, wherein the pattern of holes is arranged in a plurality of columns, each of said columns having 3-20 holes.

36. A mask assembly for treatment of obstructive sleep apnea and configured to deliver gas pressurized above atmospheric to a patient, the mask assembly comprising:
the mask frame according to claim 30; and
a cushion of silicone material separately attached to the mask frame.

37. The mask frame according to claim 30, wherein the pattern of holes includes at least six holes.

38. A mask frame assembly for a mask assembly useful for treating sleep disordered breathing of a patient, comprising: a one piece main body having a bore extending through polycarbonate material; an elbow received within the bore; and a pattern of gas washout vent holes of substantially circular cross section adapted to allow washout of gases exhaled by the patient, the pattern of holes extending through polycarbonate material of the one piece main body, each of said holes being provided on a continuous, substantially planar surface aligned between an apex of the main body and the bore, the bore being positioned below the apex, the continuous, substantially planar surface containing all of the vent holes and being laterally centered with respect to the apex, wherein at least a part of the substantially planar surface is not substantially recessed with respect to surrounding portions of the frame so as to avoid noise inducing interference between gas exiting from the holes and the surrounding portions of the frame; and wherein the substantially planar surface is positioned at a location on the main body adapted to correspond to a nasal bridge of a patient when the mask frame is positioned on a face of the patient.

39. The mask frame assembly according to claim 38, wherein the substantially planar surface is inclined with respect to vertical so that the holes are adapted to direct exhausted air upwardly and outwardly from the frame.

40. The mask frame assembly according to claim 38, wherein each hole converges from a larger diameter to a smaller diameter as viewed in the direction of exhausted gas.

41. The mask frame assembly according to claim 38, further comprising lower headgear clip attachment points adapted to be engaged with clips provided to straps of a headgear assembly.

42. A mask assembly for treatment of obstructive sleep apnea and configured to deliver gas pressurized above atmospheric to a patient, the mask assembly comprising:
the mask frame assembly according to claim 38; and
a cushion provided to the mask frame.

43. The mask frame assembly according to claim 38, wherein the pattern of gas washout vent holes is positioned on the planar surface of the main body so as to reduce noise-inducing interference between gas exiting the holes and adjacent portions of the main body.

44. The mask frame assembly according to claim 38, wherein the pattern of vent holes includes at least six holes.

45. A full face mask assembly for treating sleep disordered breathing of a sleeping patient, the mask assembly comprising: a molded polycarbonate frame; a silicone cushion attached to the frame and adapted to form a seal with the patient's face; an elbow assembly adapted to connect to an air delivery tube to deliver gas to the patient; a forehead support; and a headgear assembly, wherein the frame comprises: a main body; an upper support member that supports the forehead support; lower headgear anchor points adapted to anchor straps of the headgear assembly; a lower bore that engages the elbow; and a vent assembly positioned proximate an apex of the main body and aligned between the lower bore and the upper support member, the vent assembly comprising: a continuous vent surface proximate the apex and being inclined such that when the mask assembly is mounted on a patient's face, the vent surface faces upward and away from the patient's face; and a plurality of holes of substantially circular cross section adapted to washout gases exhaled by the patient, all of the holes being arranged in a grouping and positioned on the continuous vent surface, at least some of the plurality of holes being offset from other holes within the grouping, wherein a length of the vent surface in a direction parallel to the longitudinal axis of the frame is longer than a width of the vent surface in a direction perpendicular to the longitudinal axis of the frame, wherein at least a part of the vent surface is not substantially recessed with respect to surrounding portions of the frame so as to avoid noise inducing interference between gas exiting from the holes and the surrounding portions of the frame.

46. The mask assembly according to claim 45, wherein the vent surface is positioned at a location on the main body adapted to correspond to a nasal bridge of a patient when the frame is positioned on a face of the patient.

47. The mask assembly according to claim 46, wherein a substantially curved surface separates the lower bore and the vent surface.

48. The mask assembly according to claim 47, wherein the vent surface and the lower bore are oriented in diverging directions.

49. The mask assembly according to claim 45, wherein the upper support member comprises spaced-apart side walls.

50. The mask assembly according to claim 49, wherein an upper part of the vent surface is between spaced-apart side walls that are continuous with sides of the upper support member.

51. The mask assembly according to claim 49, wherein the vent surface is aligned between the sides of the upper support member and the sides of the upper support member are integral with the main body of the frame.

52. The mask assembly according to claim 49, wherein the vent surface is at least partially defined by the spaced-apart side walls of the upper support member.

53. The mask assembly according to claim 45, wherein the vent surface comprises a substantially planar portion having a generally oval shape.

54. The mask assembly according to claim 45, wherein the lower bore is positioned approximately between the lower headgear anchor points.

55. The mask assembly according to claim 45, wherein the grouping of holes is symmetrical about the longitudinal axis.

56. The mask assembly according to claim 45, wherein the substantially smooth, planar surface is planar.

57. The mask according to claim 45, wherein the vent surface is positioned on the main body so as to prevent noise-inducing interference between gas exiting the holes and adjacent portions of the frame.

58. The mask assembly according to claim 45, wherein the plurality of holes includes at least six holes.

59. A mask assembly for treating sleep disordered breathing of a patient, the mask assembly comprising: a molded polycarbonate frame; a cushion adapted to form a seal with the patient's face; a cushion clip that retains the cushion to the frame, the frame including a plurality of recesses to receive the cushion clip; an elbow assembly provided to the frame and adapted to connect to an air delivery tube to deliver gas to the patient; a forehead support; and a headgear assembly adapted to support the mask assembly proximate the user's face, wherein the frame comprises: a main body; a lower bore that engages the elbow; and a vent assembly adapted to allow washout of gases exhaled by the patient, the vent assembly being positioned superior to the lower bore, the vent assembly comprising: a flat and substantially smooth surface; and a plurality of holes of substantially circular cross section arranged through the flat and substantially smooth surface, wherein the holes of the vent assembly are not substantially recessed so as to avoid noise inducing interference between gas exiting from the holes and the adjacent portions of the frame.

60. The mask assembly according to claim 59, wherein the flat and substantially smooth surface is located substantially adjacent an apex of the main body.

61. The mask assembly according to claim 60, wherein the flat and substantially smooth surface is positioned at a location on the main body adapted to correspond to a nasal bridge of a patient when the frame is positioned on a face of the patient.

62. The mask assembly according to claim 61, wherein an upper part of the flat and substantially smooth surface is at least partially bounded by spaced-apart side walls.

63. The mask assembly according to claim 59, wherein a length of the flat and substantially smooth surface in a direction parallel to the longitudinal axis of the frame is longer than a width of the flat and substantially smooth surface in a direction perpendicular to the longitudinal axis of the frame.

64. The mask assembly according to claim 59, wherein the plurality of holes includes at least six holes.

* * * * *